US012577612B2

(12) United States Patent
Georgiou et al.

(10) Patent No.: US 12,577,612 B2
(45) Date of Patent: Mar. 17, 2026

(54) DEVICES AND METHOD FOR DETECTING AN AMPLIFICATION EVENT

(71) Applicant: Imperial College Innovations Limited, London (GB)

(72) Inventors: Pantelis Georgiou, London (GB); Ahmad Monirii, London (GB); Nicolas Moser, London (GB); Jesus Rodriguez Manzano, London (GB)

(73) Assignee: Imperial College Innovations Limited, London (GB)

( * ) Notice: Subject to any disclaimer, the term of this patent is extended or adjusted under 35 U.S.C. 154(b) by 1132 days.

(21) Appl. No.: 16/973,407

(22) PCT Filed: Jun. 7, 2019

(86) PCT No.: PCT/GB2019/051597
§ 371 (c)(1),
(2) Date: Dec. 8, 2020

(87) PCT Pub. No.: WO2019/234451
PCT Pub. Date: Dec. 12, 2019

(65) Prior Publication Data
US 2021/0180120 A1     Jun. 17, 2021

(30) Foreign Application Priority Data
Jun. 8, 2018     (GB) ...................................... 1809420

(51) Int. Cl.
*C12Q 1/6848* (2018.01)
*G16B 40/20* (2019.01)
(52) U.S. Cl.
CPC ........... *C12Q 1/6848* (2013.01); *G16B 40/20* (2019.02)
(58) Field of Classification Search
None
See application file for complete search history.

(56) References Cited

U.S. PATENT DOCUMENTS

| | | | |
|---|---|---|---|
| 7,680,060 B2 | 3/2010 | Jennings | |
| 7,680,868 B2 | 3/2010 | Kurnik et al. | |
| 2006/0127934 A1 | 6/2006 | Trama et al. | |
| 2007/0073489 A1 | 3/2007 | Kurnik | |
| 2014/0113357 A1 | 4/2014 | Russak | |
| 2014/0274732 A1* | 9/2014 | Hanes ................. | C12Q 1/6869 506/2 |

FOREIGN PATENT DOCUMENTS

| | | |
|---|---|---|
| CN | 105624290 A | 6/2016 |
| EP | 2272978 A1 | 1/2011 |
| WO | WO-0015849 A1 | 3/2000 |
| WO | WO 2008/107014 A | 9/2008 |
| WO | WO-2008137715 A1 | 11/2008 |
| WO | WO-2010040374 A1 | 4/2010 |
| WO | WO-2010099461 A1 | 9/2010 |
| WO | 2013008042 A1 | 1/2013 |
| WO | WO-2018027238 A1 | 2/2018 |
| WO | WO-2018070659 A1 | 4/2018 |

OTHER PUBLICATIONS

Toumazou (Nature Methods vol. 10 No. Jul. 7, 2013 pp. 641-646).*
Moser (IEEE Transactions on Biomedical Circuits and Systems vol. 12 No. Apr. 2, 2018).*
Moser ("Live demonstration: A CMOS-based ISFET array for rapid diagnosis of the Zika virus." 2017 IEEE International Symposium on Circuits and Systems (ISCAS). IEEE, May 28-31, 2017).*
European Office Action (94.3) received for EP Application No. 19731893.4 on Jan. 2, 2024, 4 pgs.
European Office Action (94.3) received for EP Application No. 19730519.6 on Jan. 10, 2024, 6 pgs.
Moser, Nicolas, et al., "A Scalable ISFET Sensing and Memory Array with Sensor Auto-Calibration for On-Chip Real-Time DNA Detection", IEEE Transactions on Biomedical Circuits and Systems, vol. 12, No. 2, Apr. 1, 2018, 12 pgs.
Salm, Eric, et al., "Electrical Detection of Nucleic Acid Amplification Using an On-Chip Quasi-Reference Electrode and PVC REFET", Analytical Chemistry, vol. 86, No. 14, Jul. 15, 2014, 8 pgs.
Toumazou, Christofer, et al., "Simultaneous DNA amplification and detection using a pH-sensing semiconductor system", Nature Methods, vol. 10, No. 7, Jul. 1, 2013, 24 pgs.
Ma Dora et al: "Adapting ISFETs for Epigenetics: An Overview" IEEE Transactions on Biomedical Circuits and Systems, IEEE, US, vol. 12, No. 5, Oct. 1, 2018 (Oct. 1, 2018), pp. 1186-1201, XP011693324, ISSN: 1932-4545, DOI:10.1109/TBCAS.2018.2838153 [retrieved on Oct. 19, 2018] the whole document.
Nicolas Moser et al: "A Scalable ISFET Sensing and Memory Array With Sensor Auto-Calibration for On-Chip Real-Time DNA Detection" IEEE Transactions on Biomedical Circuits and Systems, vol. 12, No. 2, Apr. 1, 2018 (Apr. 1, 2018), pp. 390-401, XP055617002, US ISSN: 1932-4545, DOI:10.1109/TBCAS.2017.2789161 the whole document.
Christofer Toumazou et al: "Simultaneous DNA amplification and detection using a pH-sensing semiconductor system", Nature Methods, vol. 10, No. 7, Jul. 1, 2013 (Jul. 1, 2013), pp. 641-646, XP055329877, New York ISSN: 1548-7091, DOI: 10.1038/nmeth. 2520 the whole document.

(Continued)

*Primary Examiner* — Amanda Haney
(74) *Attorney, Agent, or Firm* — Merchant & Gould P.C.

(57) ABSTRACT
A method is disclosed herein for detecting an amplification reaction in a solution containing a biological sample using an array of ion sensors. The amplification reaction is indicative of the presence of a nucleic acid. The method comprises monitoring a signal from each respective sensor of the array of ion sensors, detecting a change in the signal from a first sensor of the array of ion sensors, and comparing the signal from the first sensor with the signal of at least one neighbouring sensor, the at least one neighbouring sensor being proximate to the first sensor in the array. The method further comprises determining, based on the comparing, that an amplification event has occurred in the solution in the vicinity of the first sensor.

16 Claims, 9 Drawing Sheets

(56)                References Cited

OTHER PUBLICATIONS

Eric Salm et al: "Electrical Detection of Nucleic Acid Amplification Using an On-Chip Quasi-Reference Electrode and a PVC REFET", Analytical Chemistry, vol. 86, No. 14, Jul. 15, 2014 (Jul. 15, 2014), pp. 6968-6975, XP055329876, US ISSN: 0003-2700, DOI: 10.1021/ac500897t the whole document.

Biomedical Imaging: From Nano to Macro, 2007, Lenseigne B. et al., "Support vector machines for automatic detection o f tuberculosis bacteria in confocal microscopy images.", pp. 85-88 Whole document relevant.

Christopher Toumazou, "Simultaneous DNA amplification and detection using a pH-sensing semiconductor system" Nature Methods, vol. 10, No. 7, Jul. 2013, 4 pages.

PCT International Search Report and Written Opinion of the ISA for PCT/GB2019/051597, mailed Sep. 9, 2019, 15 pages.

GB Search and Exam Report for GB 1809420.1, dated Feb. 28, 2019, 6 pages.

Abu-Mostafa Y.S., et al., "Learning from Data", 2012, 215 pages.

Alere F., "ID Now™ Influenza A & B 2—There Is No Time Like ID Now", 2016, 1 page.

Bensimon A., et al., "Alignment and Sensitive Detection of DNA by a Moving Interface", Sep. 30, 1994, vol. 265 (5181), Retrieved from www.sciencemag.org on Dec. 20, 2014, 3 pages.

Bergveld P., "Short Communications—Development of an Ion-Sensitive Solid-State Device for Neurophysiological Measurements", IEEE Transactions on Bio-Medical Engineering, Jan. 1970, 2 pages.

Bergveld P., "Thirty Years of ISFETOLOGY: What Happened in the Past 30 Years and What May Happen in the Next 30 Years", Jan. 1, 2003, vol. 88 (1), pp. 1-20.

Berlinet A., et al., "Reproducing Kernel Hilbert Spaces in Probability and Statistics," 2004, 368 pages.

BIOFIRE® Respiratory 2.1 Plus Panel "Biofire Filmarray Respiratory Panel", 2016, 1 page.

Boyd S., et al., "Convex Optimization," Cambridge University Press, Retrieved from Internet URL: https://www.cambridge.org/in/academic/subjects/statistics-probability/optimization-or-and-risk/convex-optimization?format=HB&isbn=9780521833783, Retrieved on Mar. 2004, 730 pages.

Bustin S.A., "Quantification of mRNA Using Real-time Reverse Transcription PCR (RT-PCR): Trends and Problems," Journal of Molecular Endocrinology, 2002, vol. 29, No. 23-39, 17 pages.

Caliendo A.M., et al., "Better Tests, Better Care: Improved Diagnostics for Infectious Diseases," Clinical Infectious Diseases, 2013, vol. 57, Supplementary. 03, 32 pages.

Carmeli Y., et al., "Controlling the Spread of Carbapenemase-Producing Gram-Negatives: Therapeutic Approach and Infection Control," Clinical Microbiology and Infection, vol. 16, No. 02, Feb. 2010, 10 pages.

Cepheid "Xpert® Xpress Flu/RSV," 2016, 1 page.

Cero'N-Carrasco J.P., et al., "Electric Field Induced DNA Damage: An Open Door for Selective Mutations", May 14, 2013, vol. 49 (69), 3 pages.

Chan E.Y., et al., "DNA Mapping Using Microfluidic Stretching and Single-Molecule Detection of Fluorescent Site-Specific Tags," Jun. 2004, vol. 14 (6), 11 pages.

Chong G.M., et al., "PCR-Based Detection of Aspergillus Fumigatus Cyp51A Mutations on Bronchoalveolar Lavage: A Multicentre Validation of the AsperGenius Assay in 201 Patients with Haematological Disease Suspected for Invasive Aspergillosis," Journal of Antimicrobial Chemotherapy, Aug. 15, 2016, vol. 71, 8 pages.

"Cobas, Liat, System," Roche Diagnostics Website, Retrieved from Internet URL: https://diagnostics.roche.com/global/en/products/instruments/cobas-liat.html, Retrieved on Mar. 25, 2022, 1 page.

Coleman T.F., et al., "An Interior Trust Region Approach for Nonlinear Minimization Subject to Bounds," Computer Science Department, Cornell University, Apr. 28, 1993, 30 pages.

Coleman T.F., et al., "On the Convergence of Reflective Newton Methods for Large-Scale Nonlinear Minimization Subject to Bounds," Cornell University, Dec. 7, 1992, 36 pages.

Combined Search and Examination Report for Great Britain Application No. 1809418.5, mailed on Feb. 6, 2019, 5 pages.

Coomans D., et al., "Use of a Microcomputer for the Definition of Multivariate Confidence Regions in Medical Diagnosis Based on Clinical Laboratory Profiles," Computers and Biomedical Research, vol. 17, Jun. 8, 1983, 14 pages.

Einstein A., "Investigations on the Theory of, The Brownian Movement", Dover Publications, Inc., 1956, 11 pages.

"Electronics Letters—Special Supplement: Semiconductors in Personalised Medicine", IET Journals, Dec. 2011, 8 pages.

Em P.B., "ISFET, Theory and Practice", IEEE Sensor Conference Toronto, Oct. 2003, 26 pages.

Enzoklop "File:Polymerase Chain Reaction.svg, Polymerase Chain Reaction—PCR," 2016, 1 page.

Ferre F., et al., "Gene Quantification," Advanced Biomedical Technologies, 1998, 379 pages.

Fischler M.A., et al., "Random Sample Consensus: A Paradigm for Model Fitting with Applications to Image Analysis and Automated Cartography," Communications of the ACM, Jun. 1981, vol. 24, No. 06, 15 pages.

Freeman W.M., et al., "Quantitative RT-PCR: Pitfalls and Potential," Biotechniques, vol. 26, Jan. 1999, 12 pages.

Friedman J., et al., "The Elements of Statistical Learning, Data Mining, Inference and Prediction," Second Edition, Springer, 2001, 764 pages.

Georgiou P., et al., "ISFET Characteristics in CMOS and their Application to Weak Inversion Operation," Sensors and Actuators B, vol. 143, 2009, 7 pages.

Ghani A.C., et al., "Expanding the Role of Diagnostic and Prognostic Tools for Infectious Diseases in Resource-Poor Settings," Nature, vol. 528, Dec. 3, 2015, 3 pages.

Gingeras T.R., et al., "Fifty Years of Molecular (DNA/RNA) Diagnostics," Clinical Chemistry, vol. 51, No. 03, 2005, 11 pages.

Girones R., et al., "Molecular Detection of Pathogens in Water—The Pros and Cons of Molecular Techniques," Water Research, vol. 44, Jun. 19, 2010, 15 pages.

GOV.UK., "Carbapenemase-Producing Enterobacteriaceae: Laboratory Confirmed Cases, 2003 to 2015," Oct. 10, 2016, 3 pages.

Guescini M., et al., "A New Real-time PCR Method to Overcome Significant Quantitative Inaccuracy due to Slight Amplification Inhibition," BMC Bioinformatics, vol. 09, No. 326, Jul. 30, 2008, 12 pages.

Guescini M., et al., "Accurate and Precise DNA Quantification in the Presence of Different Amplification Efficiencies Using an Improved Cy0 Method," PLOS ONE, vol. 08, Issue. 07, Jul. 2013, 11 pages.

Heid C.A., et al., "Real Time Quantitative PCR," Genome Research, vol. 06, May 18, 2021, 10 pages.

Higuchi R., et al., "Kinetic PCR Analysis: Real-time Monitoring of DNA Amplification Reactions," BIO/Technology, vol. 11, Sep. 1993, 5 pages.

"HIV Drug Resistance Database", Stanford University, Retrieved from Internet URL: https://hivdb.stanford.edu/page/wh0-sdm-list, Retrieved on May 24, 2018, 2 pages.

Hogg R.V., et al., "Probability and Statistical Inference", Ninth Edition, 2006, 557 pages.

Hotelling H., "Analysis of a Complex of Statistical Variables Into Principal Components," Columbia University, 1933, 25 pages.

Hsieh C.C., et al., "Simulation Guided Design of a Microfluidic Device for Electrophoretic Stretching of DNA", AIP Biomicrofluidics, Oct. 24, 2012, vol. 6 (4), 13 pages.

Hu Y., "A Robust ISFET pH-Measuring Front-End for Chemical Reaction Monitoring," IEEE Transactions on Biomedical Circuits and Systems, Apr. 2014, vol. 8 (2), 9 pages.

Hud N.V., "Nucleic Acid—Metal Ion Interactions," RSC Publishing, 2009, 448 pages.

International Preliminary Report on Patentability for Application No. PCT/EP2019/065039 mailed on Dec. 8, 2020, 9 pages.

International Preliminary Report on Patentability for Application No. PCT/EP2019/065046, mailed on Dec. 8, 2020, 9 pages.

(56)　　　　　References Cited

OTHER PUBLICATIONS

International Preliminary Report on Patentability for Application No. PCT/EP2019/065047 mailed on Dec. 8, 2020, 8 pages.
International Preliminary Report on Patentability for Application No. PCT/GB2019/051597 mailed on Dec. 8, 2020, 7 pages.
International Search Report and Written Opinion for Application No. PCT/EP2019/065039 mailed on Oct. 1, 2019, 17 pages.
International Search Report and Written Opinion for Application No. PCT/EP2019/065046, mailed on Jul. 24, 2019, 15 pages.
International Search Report and Written Opinion for Application No. PCT/EP2019/065047 mailed on Sep. 10, 2019, 12 pages.
Jakobson C.G., et al., "1/f Noise in Ion Sensitive Field Effect Transistors from Subthreshold to Saturation", IEEE Transactions on Electron Devices, Jan. 1999, vol. 46 (1), 2 pages.
Kanderian S., et al., "Automated Classification and Cluster Visualization of Genotypes Derived from High Resolution Melt Curves," PLOS ONE, Nov. 25, 2015, vol. 10, No. 11, 14 pages.
Klein D., "Quantification Using Real-time PCR Technology: Applications and Limitations," Trends in Molecular Medicine, vol. 08, No. 06, Jun. 2002, 4 pages.
Lagarias J.C., et al., "Convergence Properties of the Nelder-Mead Simplex Method in Low Dimensions," Society for Industrial and Applied Mathematics, vol. 09, No. 01, Dec. 2, 1998, 36 pages.
Lee C.H., et al., "Stretching DNA by Electric Field and Flow Field in Microfluidic Devices: An Experimental Validation to the Devices Designed with Computer Simulations," Feb. 8, 2013, vol. 7 (1), 14 pages.
Lee Y., et al., "Single-Channel Multiplexing Without Melting Curve Analysis In Real-Time PCR," Scientific Reports, Dec. 11, 2014, vol. 4, 6 pages.
Levenberg K., "A Method for the Solution of Certain Non-Linear Problems in Least Squares," Quarterly of Applied Mathematics, Jul. 1944, vol. 2, No. 2, pp. 164-168.
Lim S.F., et al., "DNA Methylation Profiling in Nanochannels", Jul. 25, 2011, vol. 5 (3), 8 pages.
Liu C., et al., "Nuclemeter: A Reaction-Diffusion Based Method for Quantifying Nucleic Acids Undergoing Enzymatic Amplification", Dec. 5, 2014, 7 pages.
Lowe D.G., "Object Recognition from Local Scale-Invariant Features", Sep. 1999, 8 pages.
Lu Y., et al., "Visualized Detection of Single-Base Difference in Multiplexed Loop-Mediated Isothermal Amplification Amplicons By Invasive Reaction Coupled With Oligonucleotide Probe-Modified Gold Nanoparticles," Biosensors and Bioelectronics, Apr. 15, 2017, vol. 90, pp. 388-393.
Mackay I.M., et al., "Survey and Summary Real-Time PCR in Virology," Nucleic Acids Research, 2002, vol. 30, No. 6, pp. 1292-1305.
Maesschalck R.D., et al., "The Mahalanobis Distance," Chemometrics and Intelligent Laboratory Systems, vol. 50, 2000, 18 pages.
Malpartida-Cardenas K., et al., "Allele-Specific Isothermal Amplification Method Using Unmodified Self-Stabilizing Competitive Primers," Analytical Chemistry, Sep. 18, 2018, vol. 90, pp. 11972-11980.
Malpartida-Cardenas K., et al., "Quantitative and Rapid Plasmodium Falciparum Malaria Diagnosis and Artemisinin-Resistance Detection Using a CMOS Lab-On-Chip Platform," Biosensors and Bioelectronics, Aug. 1, 2019, vol. 145, 16 pages.
Manzano J.R., et al., "Reading Out Single-Molecule Digital RNA and DNA Isothermal Amplification in Nanoliter Volumes with Unmodified Camera Phones," ACSNANO, Retrieved from Internet URL: https://pubs.acs.org/doi/abs/10.1021/acsnano.5b07338, Retrieved on Feb. 3, 2016, 12 pages.
Marquardt D.W., "An Algorithm for Least-Squares Estimation of Nonlinear Parameters," Journal of the Society for Industrial and Applied Mathematics, Jun. 1963, vol. 11, No. 2, pp. 431-441.
Mathworks., "Supervised Learning Workflow and Algorithms," 2021, 1 page.
Mclachlan G.J., "Mahalanobis Distance," Resonance, Jun. 1999, pp. 20-26.

Michalet X., et al., "Dynamic Molecular Combing: Stretching the Whole Human Genome for High-Resolution Studies", Sep. 5, 1997, vol. 277 (5331), 7 pages.
Misyura M., et al., "Improving Validation Methods for Molecular Diagnostics: Application of Bland-Altman, Deming and Simple Linear Regression Analyses in Assay Comparison and Evaluation for Next-Generation Sequencing," Journal of Clinical Pathology (2018), Jul. 26, 2017, vol. 71, pp. 117-124.
Mohon A.N., et al., "A Novel Single-Nucleotide Polymorphism Loop Mediated Isothermal Amplification Assay for Detection of Artemisinin-Resistant Plasmodium falciparum Malaria," Open Forum Infectious disease, Jan. 9, 2018, vol. 4, No. 4, 8 pages.
Moniri A., et al., "Framework for DNA Quantification and Outlier Detection Using Multidimensional Standard Curves," Analytical Chemistry, May 6, 2019, vol. 91, No. 11, pp. 7426-7434.
Monterio., et al., "Rapid Detection of Carbapenemase Genes By Multiplex Real-Time PCR," Journal of Antimicrobial Chemotherapy, Jan. 9, 2012, vol. 67, No. 4, pp. 906-909.
Moore J.W., et al., "The Molecular Science," Chemistry 3rd Edition, 2005, 1287 pages.
Moreno A.C., et al., "Azole-resistant Aspergillus Fumigatus Harboring TR34/L98H,, TR46/Y121F/T289A and TR53 Mutations Related to Flower Fields in Colombia," Scientific Reports, vol. 07, No. 45631, Retrieved from Internet URL: https://www.nature.com/articles/srep45631, Retrieved on Mar. 30, 2017, 8 pages.
Mori Y., et al., "Real-Time Turbidimetry of LAMP Reaction for Quantifying Template DNA", Journal of Biochemical and Biophysical Methods, May 31, 2004, vol. 59 (2), pp. 145-157.
Moser., et al., "Live Demonstration: A CMOS-Based ISFET Array for Rapid Diagnosis of the Zika Virus," 2017 IEEE International Symposium on Circuits and Systems (ISCAS), May 28-31, 2017, 1 page.
Moser N., et al., "An Ion Imaging ISFET Array for Potassium and Sodium Detection," Retrieved on Jun. 26, 2021, 4 pages.
Moser N., et al., "ISFETs in CMOS and Emergent Trends in Instrumentation: A Review," IEEE Sensors Journal, vol. 16, No. 17, Sep. 1, 2016, 19 pages.
Nelder J.A., et al., "A Simplex Method for Function Minimization," The Computer Journal, vol. 7, Issue 4, Jan. 1965, pp. 308-313.
Nolan T., et al., "Quantification of mRNA using Real-Time RT-PCR," Nature Protocols, Nov. 9, 2006, vol. 1, No. 3, pp. 1559-1582.
Notomi T., et al., "Loop-Mediated Isothermal Amplification of DNA", Nucleic Acid Research, Jun. 15, 2000, vol. 28 (12), 7 pages.
Orou A., et al., "Allele-Specific Competitive Blocker PCR: A One-Step Method with Applicability to Pool Screening," Human Mutation, 1995, vol. 6, No. 2, pp. 163-169.
Otter J.A., et al., "Counting the Cost of an Outbreak of Carbapenemase-Producing Enterobacteriaceae: An Economic Evaluation From a Hospital Perspective," Clinical Microbiology and Infection, Oct. 13, 2016, vol. 23, vol. 3, pp. 188-196.
Otter J.O., et al., "Emergence and Clonal Spread of Colistin Resistance Due to Multiple Mutational Mechanisms in Carbapenemase-Producing Klebsiella Pneumoniae in London," Scientific Reports, Oct. 5, 2017, vol. 7, 8 pages.
Parida M., et al., "Loop Mediated Isothermal Amplification (LAMP): A New Generation of Innovative Gene Amplification Technique; Perspectives in Clinical Diagnosis of Infectious Diseases", 2008, vol. 18 (6), pp. 407-421.
Pearson K., "LIII. On Lines and Planes of Closest Fit to Systems of Points in Space," The London, Edinburgh, and Dublin Philosophical Magazine and Journal of Science, Jun. 8, 2010, vol. 2,Issue 11, pp. 559-572.
Phillips K.M., et al., "Application of Single Molecule Technology to Rapidly Map Long DNA and Study the Conformation of Stretched DNA," Nucleic Acids Research, Oct. 20, 2005, vol. 33 (18), pp. 5829-5837.
Purushothaman S., et al., "Protons and Single Nucleotide Polymorphism Detection: A Simple Use for the Ion Sensitive Field Effect Transistor," Apr. 2006, vol. 114 (2), 5 pages.
Randall G.C., et al., "DNA Deformation in Electric Fields: DNA Driven Past a Cylindrical Obstruction", Macromolecules, 2005, vol. 38 (6), pp. 2410-2418.

(56) References Cited

OTHER PUBLICATIONS

Randall G.C., et al., "Methods to Electrophoretically Stretch DNA: Microcontractions, Gels, and Hybrid Gel-Microcontraction Devices", Mar. 7, 2006, 10 pages.

Rao X., et al., "A New Method for Quantitative Real-Time Polymerase Chain Reaction Data Analysis," Journal of Computational Biology, 2013, vol. 20, No. 9, pp. 703-711.

Regmi S.M., et al., "Polymorphisms in Drug-Resistant-Related Genes shared Among Drug-Resistant And Pan-Susceptible Strains of Sequence Type 10, Beijing Family of Mycobacterium Tuberculosis," International Journal of Mycobacteriology, vol. 4, Issue.1, Jan. 9, 2015, pp. 67-72.

Reisner W., et al., "Statics and Dynamics of Single DNA Molecules Confined in Nanochannels", May 20, 2005, vol. 94 (19), 4 pages.

Rutledge R.G., "Sigmoidal curve-fitting redefines quantitative real-time PCR with the prospective of developing automated high-throughput applications," Nucleic Acids Research, Dec. 15, 2004, vol. 32, No. 22, 8 pages.

Saiki R.K., et al., "Enzymatic Amplification of β-Globin Genomic Sequences and Restriction Site Analysis for Diagnosis of Sickle Cell Anemia", Dec. 20, 1985, Retrieved from http://science.sciencemag.org/ on Jun. 23, 2021, vol. 230 (4732), pp. 1350-1354.

Salant H., "The Development of a Loop-Mediated Isothermal Amplification Method (Lamp) for Echinococcus Granulosis Coprodetection," Am J Trop Med Hyg, Sep. 17, 2012, vol. 87 (5), pp. 883-837.

Sekyere J.O., et al., "Review of Established and Innovative Detection Methods for Carbapenemase-Producing Gram-Negative Bacteria," Journal of Applied Microbiology, Jul. 23, 2015, 15 pages.

Sisti D., et al., Shape based Kinetic Outlier Detection in Real-Time PCR, BMC Bioinformatics, 2010, vol. 11, No. 186, 12 pages.

Song J., et al., "Molecular Detection of Schistosome Infections with a Disposable Microfluidic Cassette," PLOS Neglected Tropical Diseases, Dec. 31, 2015, 18 pages.

Spiess A., et al., "Highly accurate sigmoidal fitting of real-time PCR data by introducing a parameter for asymmetry," BMC Bioinformatics, Apr. 29, 2008, vol. 9, No. 221, 12 pages.

Subramanian S., et al., "An Empirical Approach for Quantifying Loop-Mediated Isothermal Amplification (LAMP) Using *Escherichia coli* as a Model System", Jun. 2014, vol. 9 (6), 10 pages.

Tegenfeldt J.O., et al., "The Dynamics of Genomic-Length DNA Molecules in 100-nm Channels," Jul. 27, 2004, vol. 101 (30), pp. 10979-10983.

Toumazou C., et al., "A New Era of Semiconductor Genetics Using Ion-Sensitive Field-Effect Transistors: The Gene-Sensitive Integrated Cell," Mar. 28, 2014, Retrieved from https://royalsocietypublishing.org/ on Jun. 23, 2021, 12 pages.

Van Der Maaten L., et al., "Dimensionality Reduction: A Comparative Review," TiCC TR 2009-005, Oct. 26, 2009, 36 pages.

Van Duin D., et al., "The Global Epidemiology of Carbapenemase-Producing Enterobacteriaceae," Virulence, 2017, vol. 8, No. 4, Retrieved from the Internet: https://doi.org/10.1080/21505594.2016.1222343, pp. 460-469.

Viau R., et al., "Intestinal Carriage of Carbapenemase-Producing Organisms: Current Status of Surveillance Methods," Clinical Microbiology Reviews, Jan. 2016, vol. 29, No. 1, pp. 1-27.

Who, "Dengue Guidelines for Diagnosis, Treatment, Prevention and Control," New Edition 2009, 160 pages.

Wittwer C.T., et al., "Continuous Fluorescence Monitoring of Rapid Cycle DNA Amplification," BioTechniques, Jan. 1997, vol. 22, No. 1, pp. 130-138 (7pages).

Wold S., et al., "PLS-Regression: A Basic Tool of Chemometrics," Chemometrics and Intelligent Laboratory Systems, 2001, vol. 58, pp. 109-130.

Young S.S., et al., "Deming, Data and Observational Studies—A Process Out of Control and Needing Fixing", Aug. 25, 2011, 5 pages.

Yu L.S., et al., "Rapid and Sensitive Detection of Azole-Resistant Aspergillus Fumigatus by Tandem Repeat Loop-Mediated Isothermal Amplification," The Journal of Molecular Diagnostics, Mar. 2019, vol. 21, No. 2, pp. 286-295.

Zhang C., et al., "Establishment and Application of a Real-Time Loop—Mediated Isothermal Amplification System for the Detection of CYP2C19 Polymorphisms," Scientific Reports, vol. 06, No. 26533, Jun. 1, 2016, 7 pages.

* cited by examiner (a)                              (b)

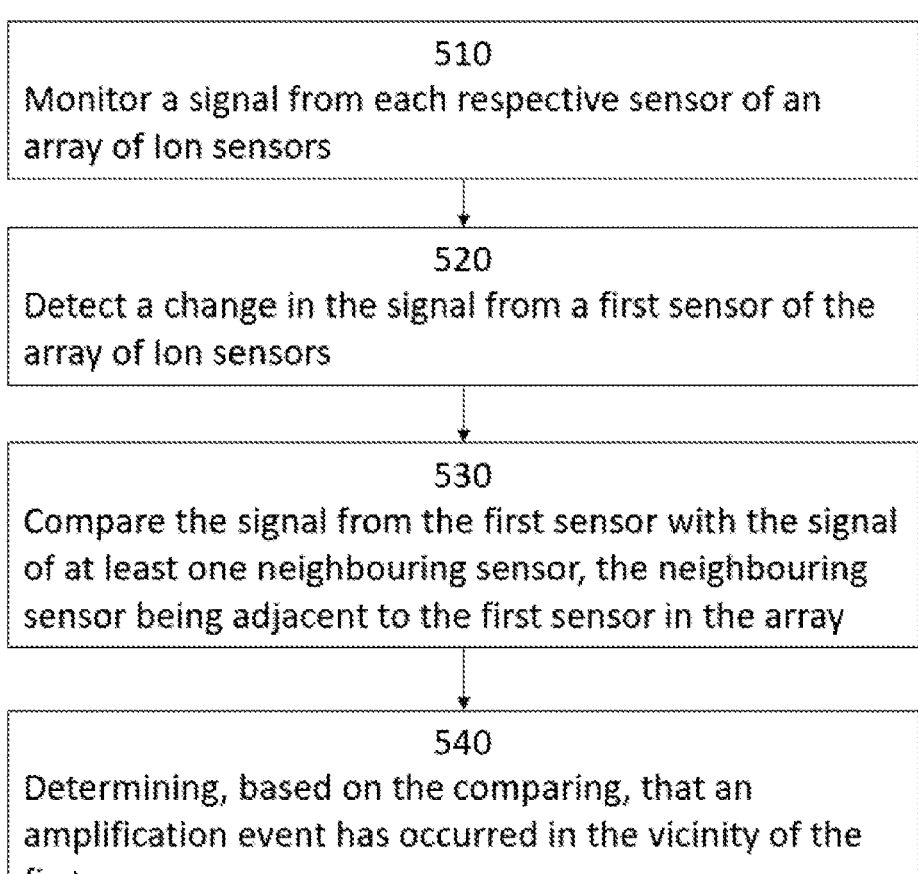

510
Monitor a signal from each respective sensor of an array of Ion sensors

520
Detect a change in the signal from a first sensor of the array of Ion sensors 530
Compare the signal from the first sensor with the signal of at least one neighbouring sensor, the neighbouring sensor being adjacent to the first sensor in the array 540
Determining, based on the comparing, that an amplification event has occurred in the vicinity of the first sensor

Fig.5

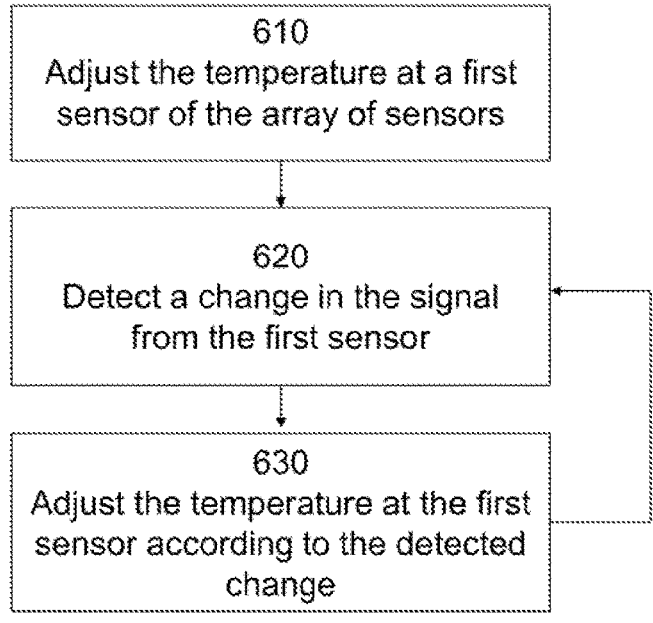

610
Adjust the temperature at a first sensor of the array of sensors

620
Detect a change in the signal from the first sensor

630
Adjust the temperature at the first sensor according to the detected change

Fig.6

Known Data ⟍
                    ⟍
                     ➔  Model
Known Responses ➔

Model ⟍
         ⟍
          ➔  Predicted Responses
New Data ➔

DEVICES AND METHOD FOR DETECTING AN AMPLIFICATION EVENT

RELATED APPLICATIONS

The present application is a National Phase entry of PCT Application No. PCT/GB2019/051597, filed Jun. 7, 2019, which claims priority from Great Britain Application No. 1809420.1, filed Jun. 8, 2018, all of these disclosures being hereby incorporated by reference in their entirety.

TECHNICAL FIELD

This disclosure relates to detecting an amplification event, and in particular to detecting an amplification reaction in a biological sample using an array of ISFET sensors.

BACKGROUND

The importance of fast, cheap, robust and quantitative detection of pathogens at the point-of-need cannot be stressed enough. However, detection of spatio-temporal chemical interactions at the molecular level, including nucleotide incorporation during nucleic acid amplification reactions and sequencing or primer-nucleic acid interactions, in real-time is not possible using current technologies without the use of high-end, expensive and bulky instruments.

Enabling these capabilities would provide fundamental insights on chemical interactions and the kinetics of biological and chemical reactions at the molecular level, such as DNA replication, DNA transcription, RNA translation or antibody-antigen binding events, and would lead to the development of more efficient detection chemistries and diagnostic methods.

There are three main classes of diagnostic methods for detection and identification of pathogens: classical microbiology techniques (such as microscopy and cultivation), protein-based (such as antigen-antibody interactions) and nucleic acid-based (such as sequencing, polymerase chain reaction and microarrays) methods. Typically, classical microbiological methods have unacceptably long cycle times and depend on visual observation. Protein-based approaches are cheap, fast, and small; however, the output is qualitative rather than quantitative, and a high concentration of pathogen in a given sample is required. By contrast, current nucleic acid-based approaches have a quantitative output, i.e. return a verdict of either present or not present, and can detect relatively low concentrations of pathogen in a given sample. However, current techniques are expensive, slow, and require large optical equipment to perform.

DNA amplification, the process of replicating DNA from one original DNA molecule, is used to amplify a single or a few copies of a segment of DNA generating thousands to millions of copies of a particular DNA sequence and can be used to determine whether a sample of human fluid or tissue contains DNA or RNA of a pathogen (such as viruses, bacteria, fungi or protozoa). The basic premise is that the DNA amplification is allowed if and only if the target pathogen exists. Following this, the DNA amplification is monitored. For instance, in traditional methods such as real-time polymerase chain reaction (PCR), each time a new amplicon is produced, a fluorescent molecule is released. Hence, the release of this fluorescent molecule is an indication of the presence of a pathogen in the sample.

It is also possible to monitor the pH of the chemical solution because during DNA amplification, each time a nucleotide is incorporated into the new DNA strand, Hydrogen ions are released which cause a change in the pH ($pH=-\log 10[H^+]$, where H+ is the concentration of Hydrogen ions or protons). The chemistry is summarized in the below equation where a is an integer constant.

$$DNA+reactants-\rightarrow 2 \cdot DNA+\alpha \cdot Proton(H+)+products$$

If DNA amplification is triggered (i.e. the pathogen is present in the sample) then the reaction is defined as positive, otherwise, the reaction is described as negative.

A high-level description of how pH-based DNA detection is typically performed is illustrated in FIG. 1a and summarized in the following steps:
1. Chemical solution consisting of sample and other necessary chemicals is prepared.
2. Amplification reagents associated with a specific pathogen are added to the solution. This consists of a primer, a sequence of bases, that complements the target DNA.
3. Depending on the method of DNA detection, the chemical solution may be heated.
4. Amplification is triggered if the primer complements the DNA in the sample.
5. DNA amplification is monitored; for instance, through fluorescence or pH.

Assuming no noise exists in the system, a typical output profile for DNA detection is shown in FIG. 1b. This figure includes a typical profile for a positive and a negative reaction. The graph shows time on the x-axis, and pH (or fluorescence) on the y-axis. The graph is split into three 'stages' representing the expected profile for DNA amplification. At stage I) the reactants have not found each other yet. At stage II) amplification is taking place. At stage III) the reaction has saturated. The 'time to positive', $t_p$, is defined as the time from the beginning of the reaction until a positive determination that the DNA is amplifying. Since the threshold is arbitrary, in examples used herein $t_p$ may be taken as the time for half of the amplification to complete.

Traditional methods of nucleic acid-based detection use optical mechanisms based on fluorescence labeling that require large and costly equipment. Typically, this equipment makes such techniques unsuitable for point-of-care diagnostics.

Polymerase chain reaction (PCR), is the most common method of nucleic acid-based detection, within which the DNA amplification is done in cycles. In each cycle, the number of DNA molecules is doubled until one of the reactants have been consumed. Each PCR cycle typically comprise three steps (denaturation, annealing and extension) and each of these steps occur at a particular temperature. PCR has an appealing property that the number of DNA molecules can be easily quantified ($2^N$, where N is the number of cycles). However, the disadvantage of PCR is that the temperature of the reaction must be controlled precisely; usually requiring a thermocycler. Ergo, PCR is unsuitable for use in point-of-care applications.

In summary, current nucleic acid-based detection methods, such as fluorescence-based techniques, are expensive, non-portable due to the need for precise temperature regulation and heavy optical equipment, do not provide spatio-temporal information, cannot be miniaturized into a small form factor device, and require a technically trained operator.

Some nucleic acid-based methods are beginning to make use of arrays of sensors. However, in previous methods, signals are gathered from each sensor in the array and, typically, a mean signal is determined which represents the signal from the entire array. The mean signal is then monitored until the threshold is reached. However, a large number of single amplification events must occur before the mean signal is significantly affected. Such approaches do not account for the fact that chemical reactions occur at local regions in solution and then spread throughout the solution as the reaction progresses. Therefore, the time taken to reach a determination in these existing methods is often significantly longer than the time taken for the first amplification event to actually occur.

The present disclosure seeks to address these and other disadvantages encountered in the prior art by providing novel technologies and methods for real-time detection of biological molecules (such as DNA, RNA and proteins). Ultimately, it is an objective of the present disclosure to improve the sensitivity and specificity of existing molecular methods, as well as to decrease the time taken to reach a positive determination while providing a quantitative result.

SUMMARY

Aspects and features of the present invention are defined in the accompanying claims.

In particular, according to a first aspect, there is provided a method for detecting an amplification reaction in a biological sample using an array of ion sensors, the amplification reaction being indicative of the presence of a pathogen. The method may comprise monitoring a signal from each respective sensor of the array of ion sensors. The method may further comprise detecting a change in the signal from a first sensor of the array of ion sensors. The method may further comprise comparing the signal from the first sensor with the signal of at least one neighbouring sensor, the neighbouring sensor being adjacent to the first sensor in the array. Even further, the method may comprise determining, based on the comparing, that an amplification event has occurred in the vicinity of the first sensor.

According to a further aspect there is provided an apparatus comprising an array of ion sensors, a processor and a memory. The memory may comprise instructions which, when executed by a processor, cause the processor to carry out the method of any preceding claim.

According to a further aspect, there is provided a computer-readable medium comprising instructions which, when executed by a processor, may cause the processor to carry out the methods of the present disclosure.

According to a further aspect, there is provided a method of use of the apparatus of the present disclosure. The method of use may comprise placing a solution containing a biological sample in contact with the array of ion sensors. The method may further comprise determining that a target molecule is present in the sample, wherein the determining comprises initiating an amplification reaction for the target molecule in the sample and detecting an amplification event.

FIGURES

Specific embodiments are now described, by way of example only, with reference to the drawings, in which:

FIG. 2a shows a typical LAMP amplification curve and FIG. 2b show a typical LAMP standard curve.

FIG. 5 is a flowchart depicting a method in accordance with the present disclosure.

FIG. 6 is a flowchart depicting a method suitable for closed-loop temperature regulation of an ISFET sensor array in accordance with the present disclosure.

DETAILED DESCRIPTION

The present disclosure relates to devices and methods that can be used in some embodiments to rapidly identify a microorganism, including a pathogen, or a cell, including a cancer cell.

Through the use of ion sensors, in particular semiconductor-based ion sensors for example the ion-sensitive field-effect transistor (ISFET), a cheap and easy-to-use diagnostic platform for chemical sensing has been designed which is suitable for point-of-care applications. The ion-sensitive field-effect transistor (ISFET) is a chemically sensitive transistor. An IFSET can be used to measure ion concentrations in solution. An array of such sensors can create a platform for chemical sensing. In some embodiments, in order to modify conventional DNA-based detection for a practical device, loop mediated isothermal amplification (LAMP) is used.

The LAMP method is an emerging method of amplification. The LAMP method is isothermal, meaning that it is carried out at a single temperature: approximately 63° C. Therefore, it is more suitable for use in point-of-care applications than PCR. It is important to note that the stages in LAMP occur in parallel and are far more complicated than in PCR. Consequently, it is not as trivial to quantify the number of nucleic acid molecules at a given instance as it is in PCR. An advantage of this method is that the amount of amplicons produced at the end of the reaction is considerably higher than PCR. This means that there is a larger pH change in LAMP (delta pH LAMP>delta pH PCR).

Figures 1A, 1B:
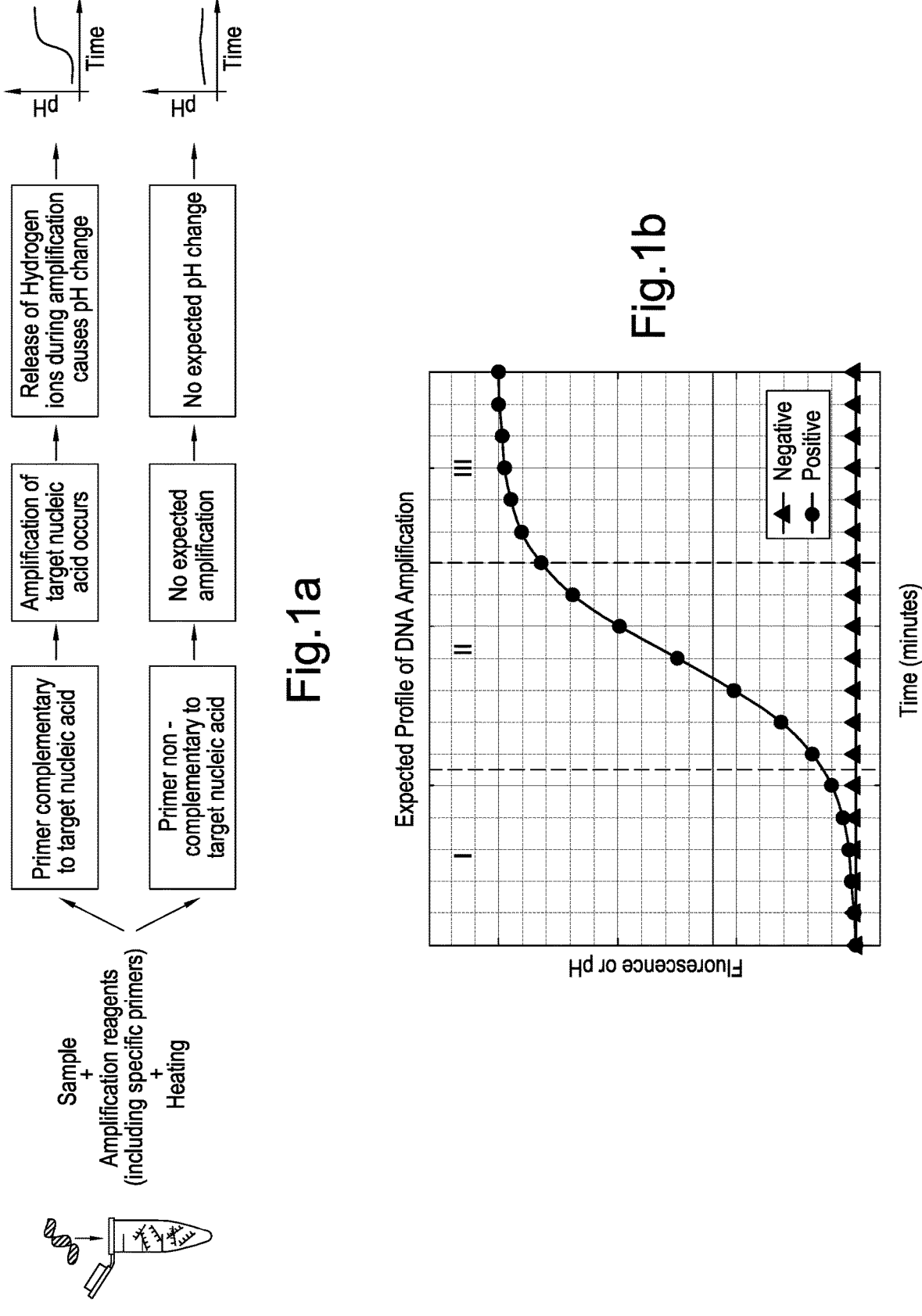
FIG. 1a depicts a typical process for pH-based nucleic acid amplification.
FIG. 1b is a graph depicting the typical profile of a negative and positive real-time amplification reaction, and in particular shows the change in pH or fluorescence over time in a DNA amplification reaction.
Figure 2:
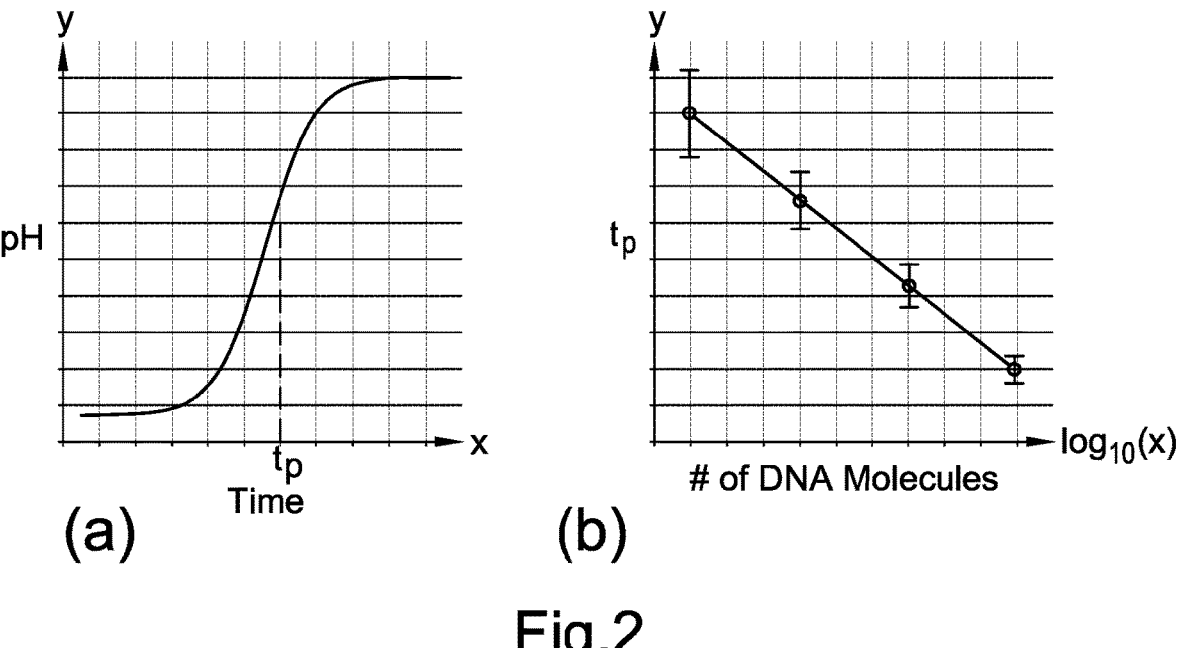
FIGS. 2a and 2b are graphs depicting global trends in a typical LAMP reaction. In particular.

FIGS. 2a and 2b depict global trends of the LAMP reaction. Time is represented on the x-axis and pH is represented on the Y axis. $T_p$ is the time to positive discussed above in relation to DNA amplification reactions generally. FIG. 2a shows how the pH in solution in which a LAMP reaction is being performed changes over time. The graph is also indicative of how the signal at a biosensor configured to detect pH changes, for example an ISFET sensor, would change over time in solution. In other words, FIG. 2a depicts the temporal nature of the signal for a LAMP experiment. FIG. 2b depicts the expected time taken to positive $t_p$ as a function of the logarithm of the number of initial molecules present in solution. This curve can be described as a calibration curve. As can be seen from the error bars in FIG. 2b, the standard deviation of $t_p$ decreases with an increasing number of initial molecules present.

Figure 3:
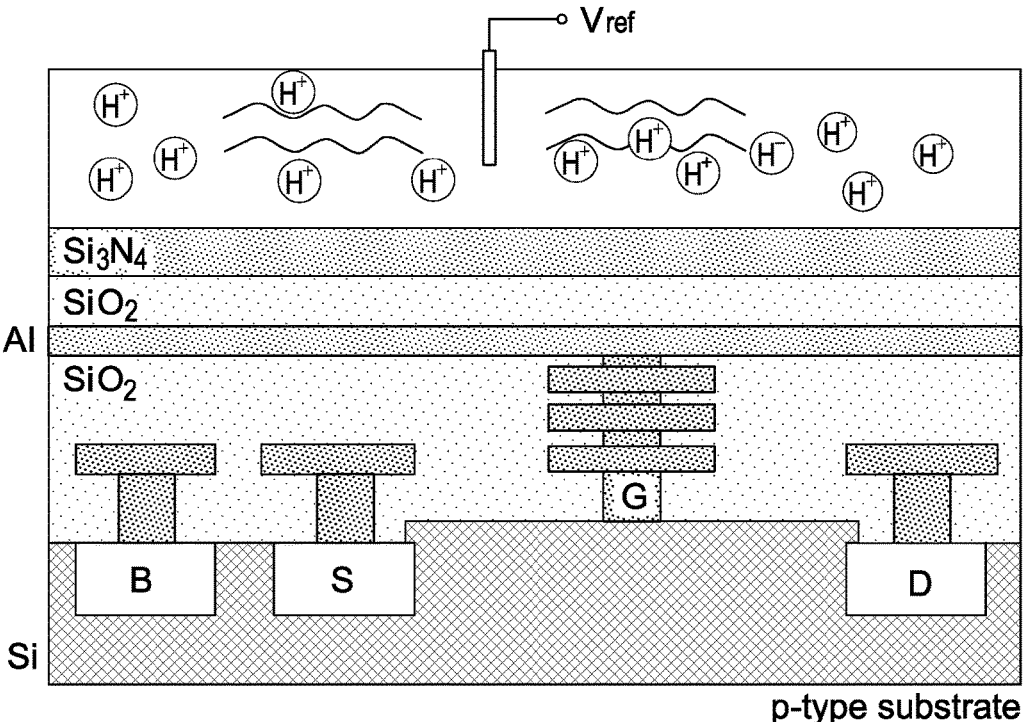
FIG. 3 shows a schematic diagram depicting a typical configuration of an ISFET sensor. In particular, a cross-section diagram of the ISFET structure in commercial CMOS (complementary metal-oxide-semiconductor) technology is depicted.

FIG. 3 is a schematic of an ISFET. The ISFET shares features and functionality with the well-known MOSFET and comprises a source, a gate, a body, a channel, and a drain. Charge carriers (e.g. electrons or holes) enter the channel at the source and exit the channel via the drain. The MOSFET works by electronically varying the effective width of the channel along which charge carriers flow by altering the voltage at the gate. This allows the voltage and current flow between the source and drain to be controlled. The voltage at the gate which is required in order for the channel to conduct charge carriers between the source and drain is called the threshold voltage. The functionality of MOSFETs will be well known to the skilled person and will not be discussed further.

The ISFET works in a similar manner to the MOSFET, and also comprises a source, drain, body, and gate. In comparison with the MOSFET, the ISFET can be modified into a biosensor by replacing the gate with a membrane in contact with a chemical solution. In this manner the number of charge carriers, i.e. ions, in the solution directly affects the device threshold voltage. The ISFET can be tailored to detect, or sense, particular chemicals and/or ions by depositing an ion-selective membrane on the gate. Insulators, such as Aluminium Oxide ($Al_2O_3$), Silicon Nitride ($Si_3N_4$), Hafnium Oxide ($HfO_2$), Tantalum Pentoxide ($Ta_2O_5$) and Silicon Dioxide ($SiO_2$), make the transistor sensitive to pH, and therefore, this makes the ISFET useful for DNA detection. The skilled person would appreciate that ISFET sensors used in the present application may take a variety of forms and configurations, and may be fabricated with negative-channel or positive-channel MOS technology. The ISFET sensors may be doped and may be of the PMOS or NMOS type.

Given that the gate of the ISFET is essentially made of the chemical solution in contact with the insulator and biased using a reference electrode, the threshold voltage of the ISFET will be sensitive to pH fluctuations, i.e. the number of protons released. Furthermore, the threshold voltage can be measured using analogue circuitry, and thus by measuring changes in the threshold voltage of an appropriately configured ISFET it is possible to detect the presence of specific ions in the solution.

Generally, the ISFET sensors may be configured to measure the pH of an electrolyte (i.e. the H+ ion content of the electrolyte), but they can be made sensitive to ions other than $H^+$ through the choice of the ion-sensitive membrane (such as $Mg^{2+}$, $Ca^{2+}$, $Na^+$ or $K^+$), thus adding an element of ion-selectivity. Unlike conventional fluorescent-based nucleic acid analysis systems, an Ion-FET based platform does not require expensive optical instruments or radioactive isotopes for detection, thus making the platform of the present disclosure a cost effective, safe and simple alternative for sensing molecules.

As discussed previously, there are several disadvantages of current nucleic acid-detection methods such as PCR. Nucleic acid-detection can be performed by running the LAMP reaction on an ISFET array in order to overcome these issues. Firstly, there is no need for a thermocycler, allowing the diagnostic platform to be portable. Secondly, there is no need for expensive optical machinery to measure fluorescence given that the ISFET array is sensitive to pH. The fact that LAMP reactions have a considerable pH change means that a detectable signal is produced from nucleic-acid amplification.

Presently disclosed methods combine the use of isothermal nucleic acid amplification reaction techniques with semiconductor-based technology, resulting in the best properties of current methods: cheap, robust, quantitative and suitable for point of care.

Figure 4:
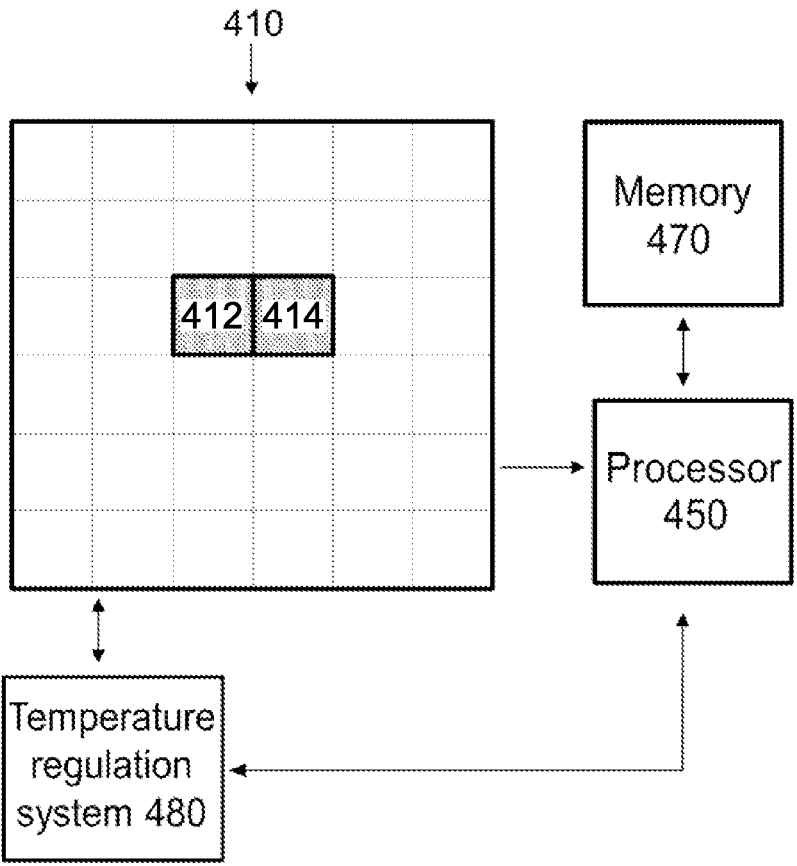
FIG. 4 depicts an apparatus including an array of sensors in accordance with the present disclosure.

FIG. 4 depicts an apparatus in accordance with the present disclosure. The apparatus comprises a processor 450. The apparatus also comprises an array 410 of ISFET sensors. The processor 450 is operably coupled/connected to each sensor in the array 410. In other words, the processor 450 is communicatively coupled to each sensor in the array 410 and can receive signals from each sensor in the array 410. The apparatus also comprises a memory 470. The processor 450 can store data in the memory 470 and also access data stored in the memory 470. Each ISFET sensor has a gate voltage electrode/reference electrode configured to be placed in a chemical solution in accordance with the operation of ISFET sensors as described above.

As will be described, the disclosed apparatus provides an integrated circuit or chip comprising a sensing platform for amplification of a target molecule (such as RNA or DNA) in a chemical sample. The integrated circuit or chip comprises the processor, memory, and a sensing platform comprising a plurality of ISFET sensors forming an array 410. The array 410 may be located within a well or chamber configured to hold the chemical sample/solution.

The array 410 of ISFET sensors comprises a plurality of ISFET sensors, including a first ISFET sensor 412 and at least one neighboring ISFET sensor 414. The first sensor 412 and the at least one neighboring sensor 414 are arranged in close proximity to one another. In other words, the first sensor 412 is in the vicinity, or neighborhood, of the second sensor 414. In some embodiments, the first and second ISFET sensors are directly adjacent to one another. In some embodiments, the first and second ISFET sensors are 'next-door-but-one' to one another. The term "neighboring" should be interpreted as meaning that the first and second sensor are proximate or relatively/substantially near to one another unless otherwise stated herein. In other words, although FIG. 4 depicts the first sensor 412 and at least one neighboring sensor 414 as being directly adjacent to one another, the skilled person would appreciate that the at least one neighbouring sensor could comprise any number of sensors in the neighbourhood of the first sensor.

The processor 450 is configured to monitor a signal from each sensor in the array 410 and is further configured to detect a change in the signal from each sensor in the array. In this way the processor is configured to detect a change in the signal from the first sensor 412. A change in the signal is associated with, and/or indicative of, a change in the number of charge carriers in the solution. The signal from a particular sensor is similarly associated with, and/or indicative of, a change in the reference voltage of the particular sensor. In some embodiments, the processor monitors the reference voltages of each of the plurality of sensors in the array 410. A change in the signal at a particular sensor is indicative of an amplification event occurring in the vicinity of that sensor, which in turn is indicative of the presence of, for example, a particular pathogen in solution.

In a preferred method of monitoring signals from the ISFET array, the signal from, for example the threshold voltage of, each ISFET sensor in the array 140 is measured in a particular pattern, and/or at a particular frequency. For example, a signal value from each sensor may be received at the processor 450 and stored in the memory 470 following a raster scan of the plurality of sensors in the array 410. The data sampling rate can be adjusted for the requirements of the particular application.

Detecting a change in the signal from a particular sensor in the array 410 may comprise comparing a current signal value from the particular sensor with at least one previously obtained signal value from the particular sensor and determining that the difference between the two values is above a predetermined threshold.

Using a plurality of ISFET sensors arranged in an array enables the extraction of not only temporal information but also spatial information. By considering spatial information, signal processing tools can be used to reduce the time to detection from the output of the ISFET array. The use of signal processing may also facilitate the real-time quantification of the reaction, that is, how much target DNA or RNA exists in the sample. This is an important step in understanding how to reduce the time taken to detect a pathogen.

Upon detecting a change in signal from the first sensor 412, the processor 450 is configured to compare the signal from the first sensor 412 with the signal from the at least one neighboring sensor 414 in the array 410. The processor 450 is further configured to determine, based on the comparing, that an amplification event has occurred in the vicinity of the first sensor. The processor 450 may be configured to perform the presently disclosed functionality using appropriate machine-readable instructions stored on an associated memory, for example the memory 470, which is accessible by the processor, as would be understood by the skilled person and as is discussed later herein.

The specifications of a suitable array of ISFET sensors are given in the table below.

| Feature | TITANICKS (2016) |
| --- | --- |
| Array Size (Total # of Sensors) | 78 × 56 |
| Number of ISFETs | 3874 |
| Number of Temperature | 494 |
| Array Dimensions | 4 mm →\| 4 mm |
| Electronic Drift Compensation | Yes |

Although FIG. 4 depicts the array 410 of sensors forming a square grid, a person skilled in the art would appreciate that the sensors could be arranged in a number of different configurations, shapes, and manners. The array 410 may be formed of a plurality of sensors so as to form a rectangle, an oval, or any other configuration which is suitable for the intended purpose discussed herein. Further, although FIG. 4 is described as comprising an array of ISFET sensors, a skilled person would appreciate that the methods and apparatus described herein could also be implemented using other kinds of sensors which are capable of detecting ions in solution.

The apparatus also comprises a temperature regulation system 480. The temperature regulation system 480 is configured to regulate the temperature of the sensors on the array 410. LAMP is an isothermal technique and the temperature regulation system 480 ensures that the sensors are kept at a relatively constant temperature. The system 480 may comprise a temperature sensing array located below and in thermal contact with the sensor array 410, as well as a heating and cooling system configured to provide heat to or take heat away from the sensor array 410. The heating cooling system may comprise a peltier system, which may be described as an active heat pump capable of transferring heat from one side of the device to the other.

The temperature regulation system 480 monitors the temperature of the sensor array 410 using the temperature sensing array, and adjusts the temperature of the sensor array 410 accordingly using the peltier system to ensure the temperature of the array is optimised optimized. This may either be in order to ensure a constant, predefined temperature (for example 63° C.) or to dynamically adjust the temperature of the sensing array 410 to ensure the rate of the reaction is optimal, as will be discussed in greater detail herein. In an example, the method comprises monitoring a temperature of the solution and/or the sensor array, and controlling a signal to heating and cooling elements, for example the heating and cooling elements of a peltier system, which are in thermal contact with the array based on the monitored temperature of the array. The heating and cooling elements may be in direct physical contact with the array and/or solution or may be otherwise in thermal contact through an intervening material or structure.

An exemplary method is depicted in the flowchart of FIG. 5. At step 510, a signal from each respective sensor from an array of ISFET sensors is monitored. As discussed above, the monitoring may comprise receiving a current signal value from each sensor and storing the current signal value in a memory. This step may comprise detecting a plurality of amplification events and monitoring the events as they occur to obtain a frequency value. The frequency value is indicative and/or associated with the number of detected reactions a second. The frequency value may be described as the rate of the reaction. The detected reactions may, or may not, be single molecule events. and wherein controlling the temperature further comprises using a closed feedback loop system to dynamically adjust the temperature based on the monitored frequency value, i.e. based on the rate of reaction. It will be appreciated that, in this manner, a closed loop feedback system is formed which may be used to ensure that the rate of reaction is optimised by adjusting the temperature of the solution and/or the array.

At step 520, a change in the signal from a first sensor of the array of ISFET sensors is detected. As discussed above, detecting a change in the signal may comprise comparing the current signal value from the first ISFET sensor to a previously obtained signal value received from the first ISFET sensor. A change in the signal received from the first sensor is indicative of an amplification event which has occurred in the vicinity of, i.e. in the neighborhood of, the first ISFET sensor.

At step 530, the signal from the first sensor is compared with the signal from at least one neighboring sensor. The neighboring sensor is nearby and/or adjacent the first sensor and therefore a change in the signal from the neighboring sensor is indicative of an amplification event in the vicinity of both the first and the neighboring sensor in the array.

At step 540, a determination is made, based on the comparison of the signal from the first sensor and the signal from the at least one neighboring sensor, that an amplification event has occurred in the vicinity of the first sensor. The determination can be made, for example, if there is a high degree of correlation between the behaviour of the signal from the first sensor and the behaviour of the signal from the at least one neighboring sensor.

Signal Processing & Machine Learning

An aim of the present disclosure is to reduce the time to detection/time to positive $t_p$ for detecting a pathogen in a sample. This problem can be described as a 'binary classification problem': the determination of whether the reaction lies on the positive or negative curve as fast as possible.

The present method comprises using machine learning algorithms to filter out detected changes in signal from sensors in the array or sensors which are unlikely to correspond to amplification events.

Traditionally, the downside of using semiconductor-based technology in nucleic acid detection was that it introduces its own challenges such as a high level of signal noise from sensor noise and drift. This has a direct impact on how fast the target nucleic acid in the sample can be detected.

In the case of ISFETs, noise is a big challenge and comes in various forms such as pink noise, sensor drift and other types of noise. In the case of the ISFET array, the signals from the vast number of sensors and the accompanying spatial information can be utilized by advanced signal processing and Machine Learning (ML) techniques to compensate for the high level of noise and to enable quick for classification of a reaction.

Given that the output of the array can be thought of as an 'image' of pH values, a single ISFET sensor is interchangeably referred to as a pixel.

Signal Noise

There are two main models for noise in semiconductor-based nucleic acid detection methods that are applicable: additive white Gaussian noise (AWGN) and sensor drift.

Additive White Gaussian Noise

Additive white Gaussian noise is a type of noise model that is used in all areas of science to mimic the effect of many random processes. Given the abundance of sources of noise, the central limit theorem indicates that the sum of all these random variables converges to a normal (also called Gaussian) distribution. The individual terms in AWGN arise due to following reasons:

1. Additive—because the noise is added onto the signal
2. White—the frequency spectrum of the noise is uniform across all frequencies[2]
3. Gaussian—because the noise is associated with a zero mean normal random variable, $X \leftarrow N(0, a^2)$ Sensor Drift During the LAMP reaction, each pixel of the ISFET array exhibits linear sensor drift. This is when the output changes independently of the input. By using algorithms or by altering the chemistry, it is possible to compensate for chemical drift. In any case, it is important to be aware of its existence.

Figures 7, 8:
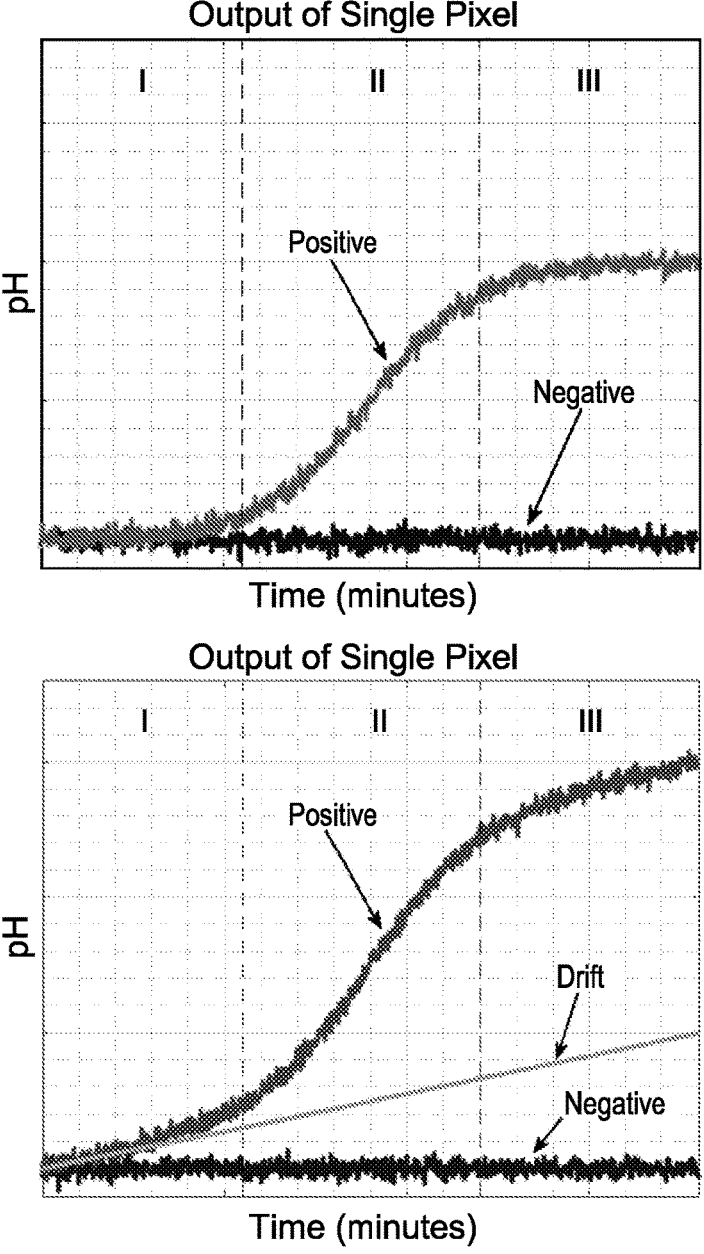
FIG. 7 depicts two graphs that show the effect of sensor drift noise on modeled output profiles of a single sensor for positive and negative amplifications reactions.
FIG. 8 is a flowchart illustration summarising some general principles of Supervised Machine Learning processes.

FIG. 7 (left plot) shows a LAMP amplification profile with AWGN and FIG. 7 (right plot) also superimposes sensor drift. Since drift is negligible in conventional methods such as PCR, it is possible to consider the left plot as the output of conventional methods and the right plot as the output of running LAMP on an ISFET array. This is an assumption made in order to formulate a realistic comparison of the time to detection between the methods when testing algorithms on the model output.

Correlation

A simple yet effective tool to extract spatio-temporal information from the array is by computing the correlation coefficient. The correlation of two sequences gives a measure of similarity. A correlation coefficient is a numerical measure of some type of correlation. In other words, the correlation co-efficient is a measure of a statistical relationship between two variables. Hence, spatio-temporal information can be observed by computing the correlation of every pixel with its neighborhood. An estimate of the correlation coefficient, $\hat{R}$, of two real sequences, x and y, is given in the below equation.

$$\hat{R}_{xy} = \sum_{n=0}^{N-1} x_n y_n$$

Using the correlation co-efficient or another similar measure of similarity between signal characteristics, the signals received from a first sensor and a nearby, neighboring sensor can be compared over time. In some examples, a first signal received from a first sensor is compared to a second signal received from a nearby sensor. This may comprise receiving a plurality of signal values from the first sensor over time. For example, a different signal/sensor value may be received by a processor at a set frequency. Similarly, signal values from the neighboring sensor are collected and monitored over time. A degree of similarity between the behavior of the signals from the respective sensors over time can be calculated and/or determined. In some embodiments, signal values from each sensor in the array are collected over time, and a degree of similarity between the characteristics of the signal received from a particular sensor compared to each of its neighboring sensors is determined. Thus, multiple degrees of similarity between the various signals of the array are determined. These degrees of similarity, in some examples correlation coefficients, can be monitored, and if signals in a particular region of the array show a similarity greater than a similarity threshold this may be indicative of an amplification reaction occurring in the vicinity of those sensors.

In disclosed methods of detecting an amplification reaction, a signal from each respective sensor of an array of ion sensors is monitored. Signals from each sensor are thus collected over time and stored in a memory. A change in the signal from a particular sensor can be detected by comparing a presently received signal from the particular sensor and comparing it to the previously received signal. In some examples, a change in signal is detected when a received signal has a value greater than a threshold value from the previously received signal, or greater than a threshold value than the mean of a plurality of previously received signals.

In some methods, as the signal from a first sensor of the array and a neighboring sensor in the array are collected/received over time, a degree of similarity between the received sets of signals is determined and constantly updated. Determining that an amplification event has occurred in the solution in the vicinity of the first sensor then may comprise detecting a change in signal value from the first sensor and also determining that a degree of similarity between the signals from the first sensor and the signals from a neighboring sensor is greater than a similarity threshold. This is indicative of an amplification reaction occurring the vicinity of the first and the neighboring sensor. As discussed, the degree of similarity may be a correlation coefficient.

In some embodiments, a degree of similarity between every sensor and its neighboring sensors is determined and constantly updated as signal values from each sensor of the array are received. Comparing the signal from the first sensor with the signal of the at least one neighboring sensor typically comprises calculating a correlation parameter between the signal of the first sensor and the signal of the at least one neighboring sensor. Determining that an amplification event has occurred may comprise determining that the degree of similarity between the signals received from the first sensor and the signals received from the neighboring sensor is greater than a similarity threshold The significance of having spatio-temporal signals can be explored using supervised ML techniques for classification.

Supervised Machine Learning

Supervised machine learning is a subset of ML where known data is available to train a model for classifying an unknown signal. This process is illustrated in FIG. 8. Machine learning is typically considered to be a black box approach as the data itself determines the parameters of the model. Tuning an ML algorithm based on observing the data is generally considered bad practice and is termed 'data snooping.

The main hurdle for ML algorithms is the ability to actually learn. If one ML algorithm works, this typically means that many other algorithms will also work. For each application, different ML algorithms exhibit slightly better performance. Examples of supervised machine learning algorithms for a classification problem relevant to this project include: Nearest Neighbors (NN), K-means clustering, Support Vector Machine (SVM), Deep Neural Networks and Randomized Decision Forest.

Application of Signal Processing Techniques

Arrays of thousands of sensors allow observation of multiple amplification events over many points. Common patterns found during the initiation phase of amplification are mathematically described by algorithms, effectively identifying patterns in the noise, improving signal-to-noise ratio and decreasing reaction time.

Mathematical models and signal processing algorithms for bulk Reverse transcription loop-mediated isothermal amplification (RT-LAMP) describe the kinetics of the amplification at single-molecule level and the release of protons from each amplification event.

Figure 9:
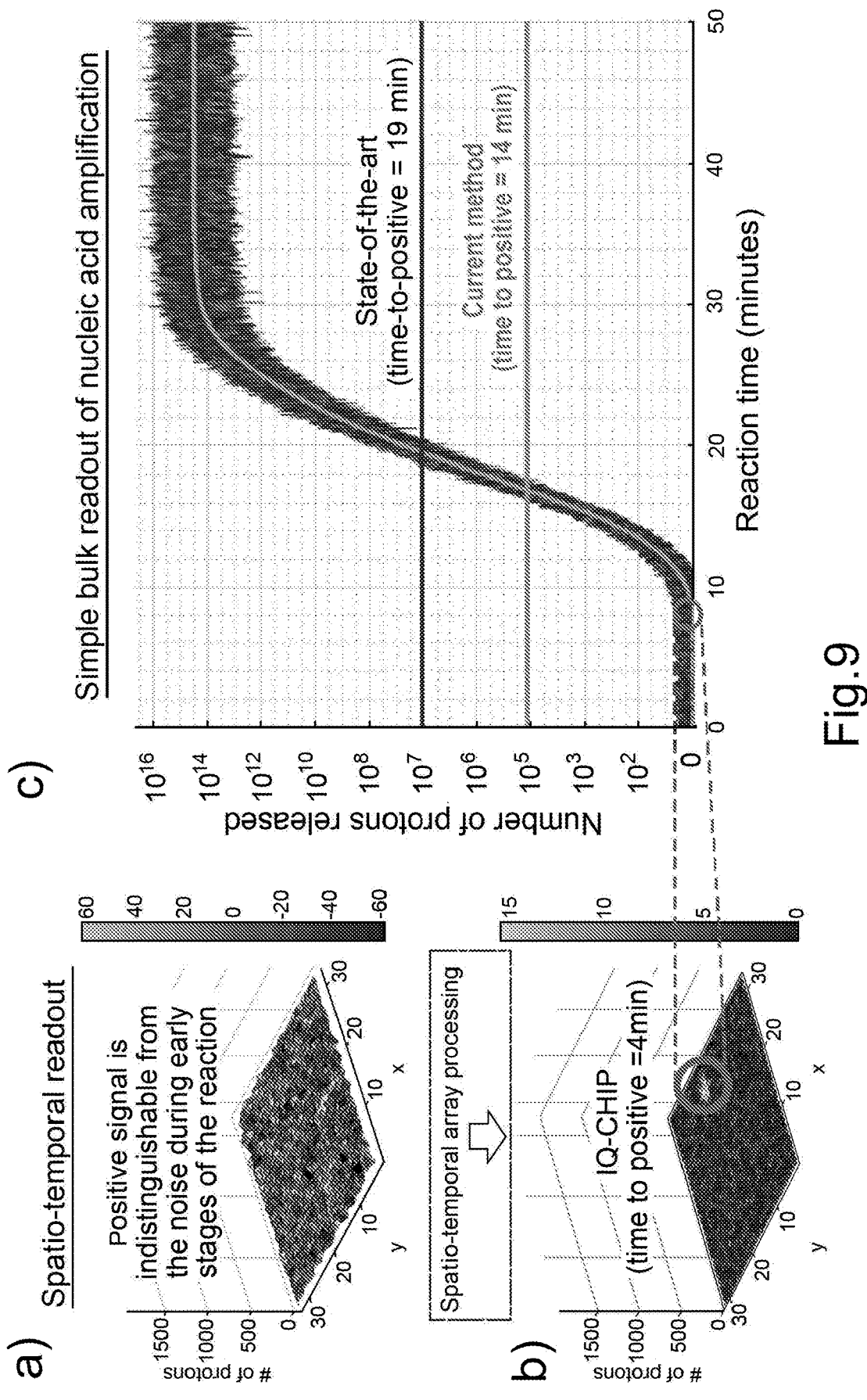
FIG. 9 illustrates the difference in time to positive results between current methods of DNA detection, which produce temporal output profiles, and the method of the present disclosure, which outputs spatio-temporal signals.

FIG. 9 shows a comparison of estimated time-to-positive reaction based on spatio-temporal and bulk readout analysis. Graphs (a) and (b) showing simulated spatio-temporal readout from proton ions released after one minute of amplification reaction in a CMOS ion-FET array (1,024 sensors array); (c) showing the time to positive compared to the state of the art on a simulate amplification reaction profile.

a) During early event of amplification (<5 min) a positive reaction signal is indistinguishable from the Poissonian-Gaussian noise, which is expected from any biosensing system;

b) Spatio-temporal averaging of pixel intensity allows the discrimination of a positive amplification reaction at 4 minute reaction time;

c) Simulated bulk readout from proton ions released during 50 minutes amplification reaction in CMOS Ion-FET. Conventional Real-Time PCR instruments (state-of-the-art) need $10^5$ amplified amplicons (equivalent to $10^7$ protons released in this figure) to have a signal from a positive amplification reaction that would cross the background noise and could be seen by optical sensors (fluorescence-based), which translates into a time-to-positive reaction of 19 min.

Current read-out methodology is able to capture 0.01 mV changes, which translate into $10^5$ protons at pH 9 and a time-to-positive of 14 min. The mathematical model developed to generate this data is based on the following parameters: i) amplification chemistry=LAMP; ii) initial number of DNA molecules=100 (random distribution in 3D space); iii) reaction volume=5 microliter; iv) front velocity of release of protons=1.8.

Spatio-Temporal Algorithms

Figures 10, 11:
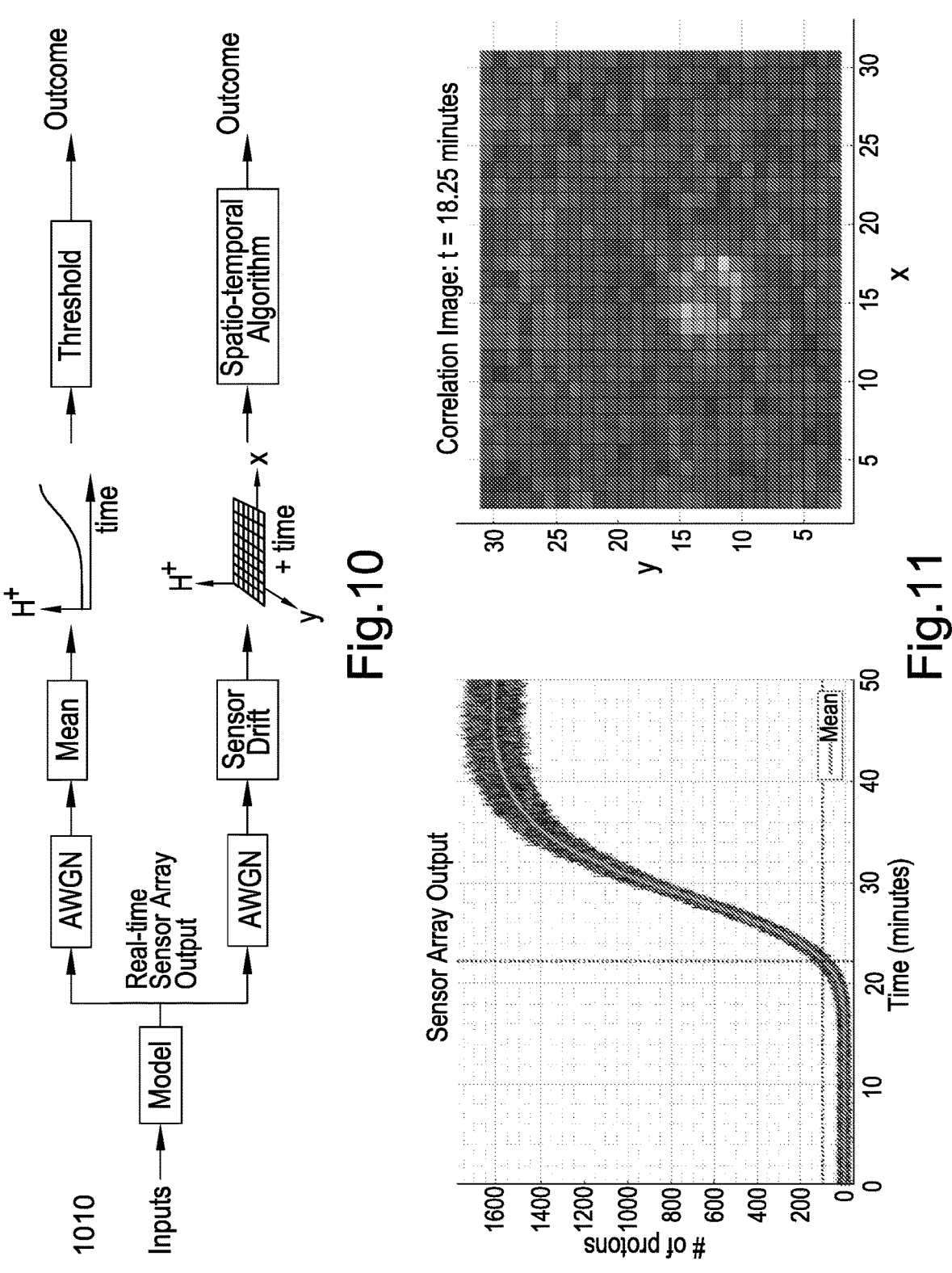
FIG. 10 depicts the broad difference between present methods of performing LAMP on an ISFET array and processing signals from the ISFET sensor array and prior methods which made use of a sensor array.
FIG. 11 depicts graphs showing a modeled positive amplification reaction profile using conventional temporal data and using spatio-temporal data in accordance with embodiments of the present disclosure.

FIG. 10 depicts the broad difference between present methods of performing LAMP on an ISFET array and processing signals from the ISFET sensor array and prior methods which made use of a sensor array. It is important to understand that noise in these systems is different, and the output signal from both systems are different. At step 1010, input is received and may be fed into a mathematical model. The common noise in both systems can be modeled as additive white gaussian noise (AWGN). In previous methods, the mean of all sensor signals is taken and plotted over time until a threshold pH is reached. The time taken to meet this threshold is the time-to-positive $t_p$.

By contrast, in the present methods, after an additional type of noise has been addressed, i.e. sensor drift, a spatio-temporal algorithm is used to indicate whether DNA amplification is occurring. The spatio-temporal algorithm can make this determination with a much shorter time to positive. Sensor drift can be modeled by adding a linear curve to each pixel where the gradient of the line is randomly chosen in the interval [0,m]: where m is approximately 20% of the number of protons at saturation.

Before exploring sophisticated algorithms, it is reasonable to first conduct a preliminary test in order to investigate why spatio-temporal algorithms should reduce the time to detection. To do this, consider the following real-time algorithm that uses a simple tool, namely correlation, to extract spatio-temporal patterns. There are two inputs: the output of the model with AWGN and sensor drift and the horizon. The horizon is the number of past data frames the algorithm considers to determine the outcome at the current time instance.

---

Algorithm 1

---

Using spatio-temporal correlation to detect regions of activity in real-time
Inputs: Estimate of ISFET Array Output and Horizon
    while Reaction is in progress do
      Store frames over the horizon;
    for Each pixel do
      Calculate correlation with 3 × 3 neighbourhood
    end for
    Detect if regions of activity exist;
end while

---

Using the aforementioned test procedure, the estimate of the signal obtained from conventional methods is shown in FIG. 11a (left plot). By applying the definition of time to positive, $t_p$ is approximately 30 minutes. If the threshold is generously reduced to the point at which amplification is visually noticed, then $t_p$=22 minutes. After applying the real-time algorithm using correlations over a horizon of 3 frames, FIG. 11b (right plot) shows the correlation image at 18.25 minutes. There is clearly a region of activity which implies DNA amplification. This 'algorithm 1' shows that the correlation image forms an object, as can be seen in FIG. 10b. It is possible to use a supervised machine learning algorithm that tunes itself to detect such patterns automatically.

Support Vector Machine

Support vector machines (SVM) are supervised machine learning models. They comprise learning algorithms that analyze data. The SVM is given a set of training examples, each marked as belonging to one or the other of two categories, and an SVM training algorithm builds a model that assigns new incoming data examples to one category or the other. It is a common and robust algorithm for binary classification such as the problem of interest.

It is simple to provide training data which is in either the positive or negative category by controlling the presence of, for example, a particular pathogen in the biological sample/chemical solution.

Figure 12:
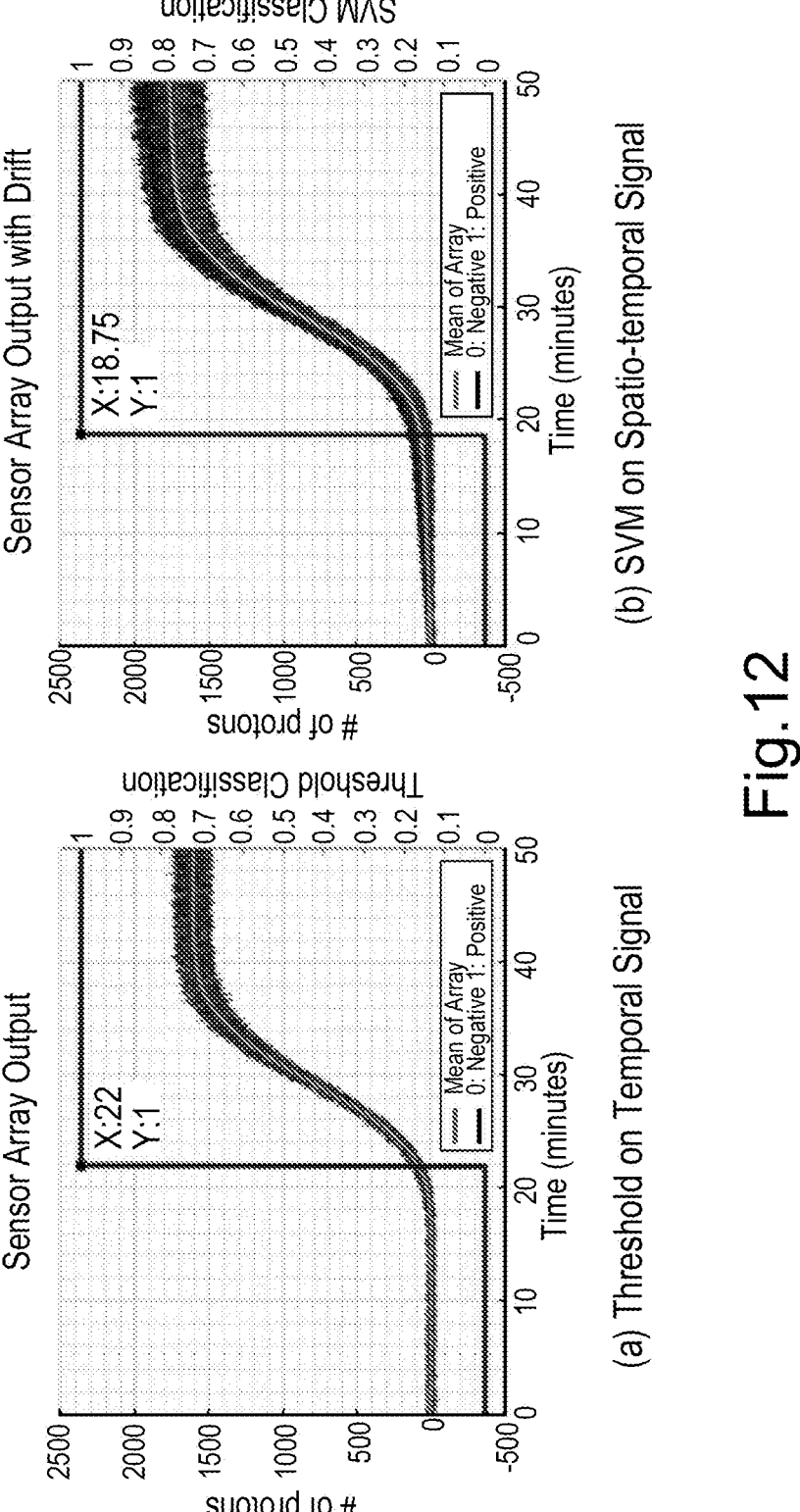
FIG. 12 depicts a modeled output of a positive amplification reaction using Support Vector Machines.

The algorithm finds patterns in the data by transforming the data into a higher dimension to find intricate patterns so taking correlations is not necessary. FIG. 12$b$ (right plot) shows the resulting prediction of a simple SVM when the raw spatio-temporal signal for 10 initial DNA molecules is fed into the SVM in real-time. This particular SVM was trained with 15 runs of the model with 10 initial molecules, AWGN with $\sigma^2=100$ and sensor drift. The corresponding conventional threshold for the same test signal is given in FIG. 12$a$ (left plot).

Figure 13:
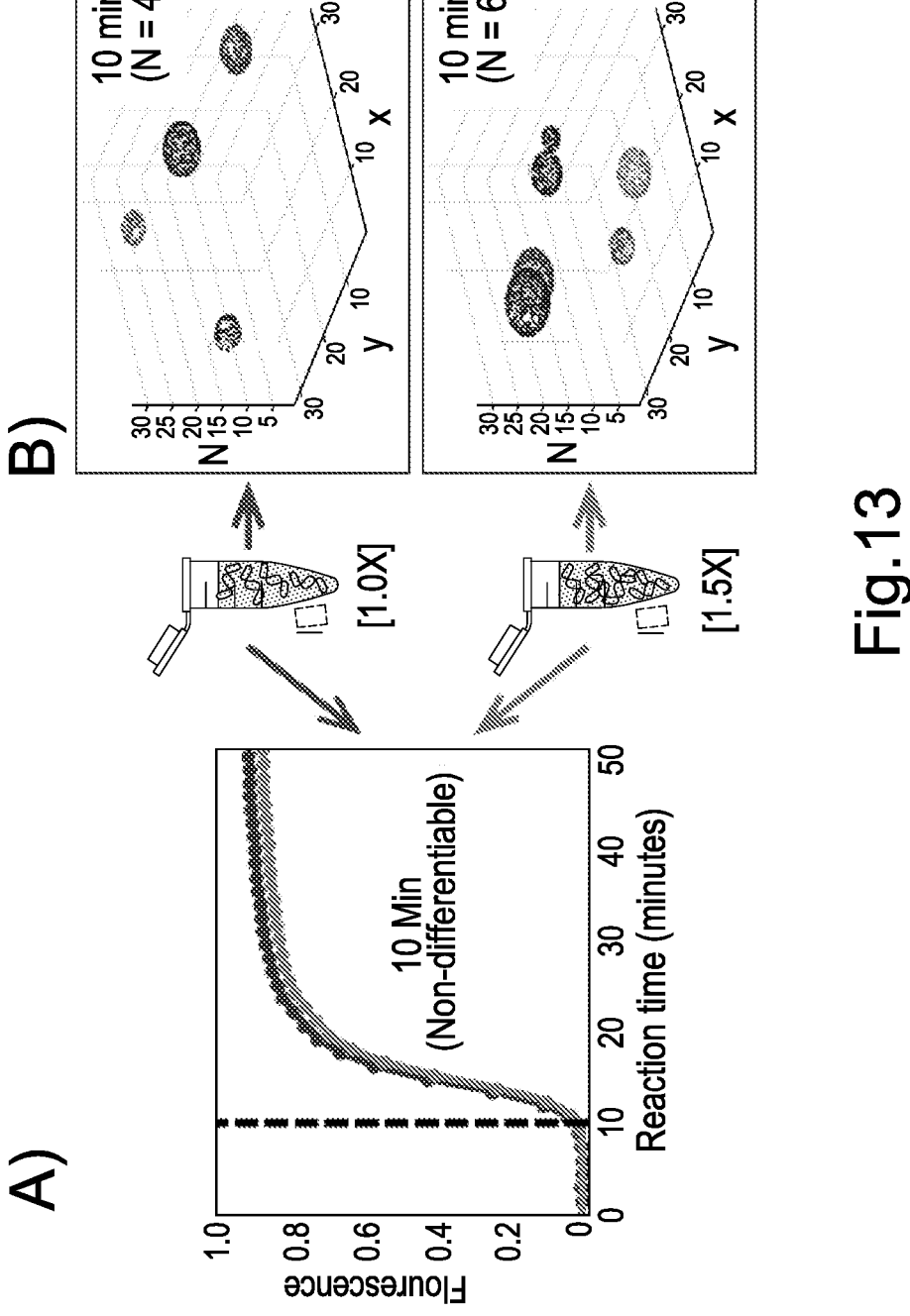
FIG. 13 depicts an overview of spatio-temporal digital quantification of nucleic acids compared to conventional real-time bulk quantification.

FIG. 13 provides an overview of spatio-temporal digital quantification of nucleic acids compared to conventional real-time bulk quantification. The illustration of the curves in the kinetic format are drawn to resemble a specific case of real-time nucleic acid amplification.

In FIG. 13$a$, in a conventional real-time format, the analyte is amplified in a bulk reaction and the progress of the amplification, measured as fluorescence, is monitored as a function of time. The original concentration is determined by comparing the reaction trace to standard curves from solutions of known concentration. After 10 minutes of reaction, the fluorescent signal has barely increased and reaction traces from 1.0× sample and 1.5× sample are indistinguishable, which means that by this method cannot capture the 0.5-fold difference in concentration.

In FIG. 13$b$ in a spatio-temporal digital format of the present invention, the analyte is amplified in a bulk reaction on top of the sensing array of the present invention and the progress of the reaction of the amplification, measured as protons released or delta pH, is monitored spatially and over time across the sensing area. This method enables identification of the signal originated from every amplified molecule. The original concentration is calculated by capturing the frequency and number of molecules that produce signal, determining the absolute concentration of analytes without the need of cycle thresholds or reference standards. In addition, the spatio-temporal digital approach enables quantification of very small changes in template concentration.

The approaches described herein may be embodied on a computer-readable medium, which may be a non-transitory computer-readable medium. The computer-readable medium carrying computer-readable instructions arranged for execution upon a processor so as to make the processor carry out any or all of the methods described herein.

The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

It will be understood that the above description of specific embodiments is by way of example only and is not intended to limit the scope of the present disclosure. Many modifications of the described embodiments, some of which are now described, are envisaged and intended to be within the scope of the present disclosure.

In some embodiments, a dynamic temperature adjustment method is utilised. Small changes in the assay temperature impact amplification efficiency. Annealing temperatures above the estimated temperature of the primers reduce efficiency and increase specificity, while annealing temperature below the estimated temperature of the primers produce the opposite effect. If the annealing temperature is too high, primers are unable to bind the template (resulting in false negative reactions). If the annealing temperature is too low, primer bind non-specifically to the template (resulting in false positive reactions).

In disclosed methods, real-time temperature adjustments are performed based on the kinetics of the reaction as a closed-loop system.

For example, an isothermal amplification reaction is monitored in real-time by the sensing array and temperature of the assay is simultaneously adjusted (e.g. around optimal annealing and extension temperatures) based on the amount of protons that are released per unit of time, increasing the efficacy of the amplification reaction.

An example method is detailed in FIG. 6. At step 610, the temperature at a first sensor of the array of sensors is adjusted. The adjustment may be on the order of 0.1 of a degree Celsius, for example.

The temperature adjustment of the first sensor may be part of a wider temperature adjustment, for example of a particular region of the array of even the entire array. At step 620, a change in the signal from the first sensor is detected, for example using methods in accordance with the methods disclosed elsewhere herein. The change in signal may suggest that the rate of reaction has increased or decreased in the vicinity of the first sensor.

At step 630, the temperature of the first sensor is adjusted based on, or according to, the detected change in signal at the first sensor. For example, if the adjusted temperature at 610 is an increase in temperature that results in a detected signal from the first sensor at 620 that suggests that the rate of reaction has increased in the vicinity of the first sensor, then the temperature can be further increased at 630.

The steps of 620 and 630 form a closed-loop feedback system in which the temperature of the first sensor, or a group or region of sensors of the array, is adjusted, the subsequent signal from these sensors is received at and detected by a processor, and the temperature can be adjusted again based on the received signal.

According to the method presented in FIG. 6, real-time, dynamic temperature adjustment of the sensor array can be achieved based on the kinetics of the reaction as a closed-loop system.

Several examples and advantages of the apparatus are now described.

In an example, the disclosed apparatus and method can enable phenotypic detection and metabolic profiling of drug resistance using individual microorganisms or cells which can be originated from various sample types, including clinical or environmental samples. These samples types can include, but are not limited to, blood, cerebral spinal fluid, saliva, urine, respiratory specimens and can also include environmental samples, such as water and sewage.

The disclosed apparatus can also be used to obtain sequencing information and/or to quantify nucleic acid molecules starting from as few as a single molecule. In some embodiments, devices and methods herein described can be performed without requiring a centralized laboratory facility, trained technicians, sample preparation, refrigeration, and/or other resources.

Disclosed methods allow genetic analysis where there is generally a need to amplify the number of copies in the sample, as the number present in the sample is generally too low to be detected. This can be done using, for example, thermocycling or isothermal amplification. Isothermal techniques include LAMP, NASBA, RPA, HDA, SDA, SMAP, ICAN, SMART. Isothermal amplification reactions proceed at constant temperature and amplification can be completed in a single step.

The disclosed devices and methods enable spatio-temporal chemical imaging at the molecular level, allowing the identification of single molecule events and therefore allowing single molecule counting (such as absolute quantification of nucleic acids and/or proteins): spatio-temporal digital quantification.

The disclosed methods allow single-molecule counting to provide ultra-sensitive measurements that improve detection limits while providing quantitative data. In some examples, the devices capture the frequency and number of single-molecule events in the reaction (such as monitoring changes in concentration of protons and/or any other ions presents in an amplification reaction), determining the absolute concentration of molecules (such as nucleic acids molecules or proteins) without the need, for example, of cycle threshold or reference standards. The sensing and actuation platform ISFET array enables ultrafast detection and digital quantification of molecules (such as nucleic acids or proteins) on a chip.

In some embodiments, the use of a sensing platform with an array of thousands of ISFET sensors enables the observation of chemicals reactions and interaction among molecules over many points across the sensing array. In some embodiments, chemical patterns produced during those chemical reactions (such as amplification of nucleic acids) and/or interaction among molecules (such as binding events) are mathematically described by algorithms which are used to identify real signals from the background noise, improving signal-to-noise ratio and decreasing reaction time and/or time to positive reaction. In some embodiments algorithms are applied to find patterns in the noise using correlation during the early stages of the chemical reaction (such as the initiation phase of a nucleic acid amplification reaction) which decreases the overall time-to-positive-signal.

In some embodiments, real-time spatio-temporal imaging of chemical patterns is captured by the sensing array in the 2D plane and it can be used to monitor and/or describe the chemical and/or biological reactions in the 3D plane, describing the kinetics of the reaction that is being imaged and enabling spatio-temporal digital quantification.

In some embodiments, the sensing platform comprises heating and/or cooling elements (such as a Peltier). In some embodiments the sensing platform comprises temperature controllers (such as proportional-integral-derivative controllers).

By measuring real-time spatio-temporal chemical images of nucleic acid interactions at the molecular level, it is possible to capture the frequency and number of single molecule amplification events in a bulk reaction (i.e., by the direct release of protons), determining the absolute concentration of nucleic acid molecules present in the reaction.

The apparatus may include a processor or a processing device, a main memory (e.g., read-only memory (ROM), flash memory, dynamic random access memory (DRAM) such as synchronous DRAM (SDRAM) or Rambus DRAM (RDRAM), etc.), a static memory (e.g., flash memory, static random access memory (SRAM), etc.), and a secondary memory (e.g., a data storage device), which communicate with each other via a bus.

The processor represents one or more general-purpose processors such as a microprocessor, central processing unit, or the like, or may be one or more special-purpose processing devices such as an application specific integrated circuit (ASIC), a field programmable gate array (FPGA), a digital signal processor (DSP), network processor, or the like. Processing device XX02 is configured to execute the processing logic (e.g. machine-readable instructions) for performing the operations and steps discussed herein.

The memory may comprise one or more machine-readable storage media (or more specifically one or more non-transitory computer-readable storage media) on which is stored one or more sets of instruction embodying any one or more of the methodologies or functions described herein.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

The methods disclosed herein may be performed using complementary metal-oxide-semiconductor (CMOS) circuitry implemented on the chip itself. The methods may be implanted using machine learning techniques created on and run on the chip. Alternatively or additionally, instructions for performing the method may be stored on the cloud.

Unless specifically stated otherwise, as apparent from the following discussion, it is appreciated that throughout the description, discussions utilizing terms such as "receiving", "determining", "comparing", "enabling", "maintaining," "identifying," "monitoring" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The skilled person will appreciate that in methods of the present disclosure, the ions in solution could be protons, or other ions such as $Mg^{2+}$, $K^+$, $Na^+$ and $Ca^{2+}$ and byproducts (such as pyrophosphate).

While LAMP methods and isothermal reactions have been discussed, it will be appreciated that non-isothermal methods may be used, such as PCR, RT-PCR qPCR, RT-qPCR nPCR, RT-nPCR, mPCR and RT-mPCR, as well as other non-LAMP isothermal methods, such as RT-LAMP, NASBA, RPA, RT-RPA, HDA, and RCA.

Disclosed herein is a method for detecting an amplification reaction in a solution containing a biological sample using an array of ion sensors, the amplification reaction being indicative of the presence of a nucleic acid. The skilled person, upon reading this disclosure, will appreciate that the nucleic acid may be, for example, DNA or RNA from a cell which is indicative of a pathological condition. The nucleic acid may comprise a sequence encoding a gene with a particular pathology-causing or pathology-associated mutation or polymorphism. The nucleic acid may be a pathogenic nucleic acid.

In embodiments in which the amplification reaction is indicative of the presence of a pathogen, a method of diagnosing a subject can be performed. The subject may be described as an entity. The subject may for example be an animal or a human patient. The subject may alternatively be a plant or plant matter. In short, the subject may be any living or non-living entity which produces nucleic acids. The method of diagnosing the subject comprises diagnosing the subject based on the presence of a pathogen. The method may comprise using the apparatus and methods detailed herein to determine and/or detect the presence of an amplification reaction which is indicative of the presence of a pathogen. The method may comprise bringing a solution containing a biological sample into contact with the array of ion sensors, determining that an amplification event indicative of the presence of a particular pathogen has occurred in the vicinity of the first sensor, and determining that the patient has a particular disease based on the presence of the pathogen.

The sample may be any suitable sample comprising a nucleic acid. For example, the sample may be an environmental sample or a clinical sample. The sample may also be a sample of synthetic DNA (such as gBlocks) or a sample of a plasmid. The plasmid may include single a nucleotide, a gene or a gene fragment of interest.

The environmental sample may be a sample from air, water, animal matter, plant matter or a surface. An environmental sample from water may be salt water, brackish water or fresh water. For example, an environmental sample from salt water may be from an ocean, sea or salt marsh. An environmental sample from brackish water may be from an estuary. An environmental sample from fresh water may be from a natural source such as a puddle, pond, stream, river, lake. An environmental sample from fresh water may also be from a man-made source such as a water supply system, a storage tank, a canal or a reservoir. An environmental sample from animal matter may, for example, be from a dead animal or a biopsy of a live animal. An environmental sample from plant matter may, for example, be from a foodstock, a plant bulb or a plant seed. An environmental sample from a surface may be from an indoor or an outdoor surface. For example, the outdoor surface be soil or compost. The indoor surface may, for example, be from a hospital, such as an operating theatre or surgical equipment, or from a dwelling, such as a food preparation area, food preparation equipment or utensils. The environmental sample may contain or be suspected of containing a pathogen. Accordingly, the nucleic acid may be a nucleic acid from the pathogen.

The clinical sample may be a sample from a patient. The nucleic acid may be a nucleic acid from the patient. The clinical sample may be a sample from a bodily fluid. The clinical sample may be from blood, serum, lymph, urine, faeces, semen, sweat, tears, amniotic fluid, wound exudate or any other bodily fluid or secretion in a state of heath or disease. The clinical sample may be a sample of cells or a cellular sample. The clinical sample may comprise cells. The clinical sample may be a tissue sample. The clinical sample may be a biopsy.

The clinical sample may be from a tumor. The clinical sample may comprise cancer cells. Accordingly, the nucleic acid may be a nucleic acid from a cancer cell.

The sample may be obtained by any suitable method. Accordingly, the method of the invention may comprise a step of obtaining the sample. For example, the environmental air sample may be obtained by impingement in liquids, impaction on solid surfaces, sedimentation, filtration, centrifugation, electrostatic precipitation, or thermal precipitation. The water sample may be obtained by containment, by using pour plates, spread plates or membrane filtration. The surface sample may be obtained by a sample/rinse method, by direct immersion, by containment, or by replicate organism direct agar contact (RODAC).

The sample from a patient may contain or be suspected of containing a pathogen. Accordingly, the nucleic acid may be a nucleic acid from the pathogen. Alternatively, the nucleic acid may be a nucleic acid from the host.

The pathogen may be any entity comprising a nucleic acid. The pathogen may be a eurkaryote, a prokaryote or a virus. The pathogen may be an animal, a plant, a fungus, a protozoan, a chromist, a bacterium or an archaeum.

Methods of the present disclosure may be used at the point of care. A blood sample may be taken from a human patient. Methods of the present disclosure are used to quickly and quantitatively determine that an amplification event has occurred in a solution containing the blood sample. The amplification event may be indicative of the presence of a particular pathogen, for example the zika virus. Based on this determination, the patient may be diagnosed with the Zika virus. Cheap, quick, and efficient diagnosis at the point of care using the present methods cannot be achieved using currently known techniques and apparatus.

The method of diagnosis may be an in vitro method or an ex vivo method.

The above implementations have been described by way of example only, and the described implementations and arrangements are to be considered in all respects only as illustrative and not restrictive. It will be appreciated that variations of the described implementations and arrangements may be made without departing from the scope of the invention.

The invention claimed is:

1. A method for detecting an amplification reaction in a solution containing a biological sample using an array of ion sensors, a processor operably coupled to the array of ion sensors, and a memory operably coupled to the processor, the amplification reaction being indicative of a presence of a nucleic acid, the method comprising:

receiving, by the processor and throughout an amplification reaction, a signal from each respective sensor of the array of ion sensors;

storing, by the processor, each signal received from each respective sensor of the array of ion sensors in the memory;

detecting, by the processor and in real time, a change in the signal from a first sensor of the array of ion sensors by comparing a current signal value received from the first sensor to at least one previously obtained signal valve received from the first sensor and stored in the memory;

comparing, by the processor and upon detecting a change in the signal from the first sensor, the signal from the first sensor with the signal of at least one neighboring sensor, the at least one neighboring sensor being proximate to the first sensor in the array wherein comparing the signal from the first sensor with the signal of the at least one neighboring sensor comprises calculation of a correlation parameter between the signal of the first sensor and the signal of the at least one neighboring sensor; and determining, by the processor and based on the correlation parameter, that an amplification event has occurred in the solution in the vicinity of the first sensor.

2. The method of claim 1, wherein the amplification event comprises a single molecule amplification event.

3. The method of claim 1, further comprising detecting a plurality of amplification events, and monitoring the events as they occur to obtain a frequency value indicative of the rate of the reaction.

4. The method of claim 3, wherein the amplification events are single molecule events and monitoring the events as they occur comprises counting the single molecule events.

5. The method of claim 1, wherein detecting a change in the signal from the first sensor comprises comparing the received signal from the first sensor to a previously received signal from the first sensor and determining that a change in signal value between the received signal and previously received signal is greater than a threshold value.

6. The method of claim 1, wherein comparing the signals comprises monitoring a degree of similarity between the signals received from the first sensor and the signals received from the neighboring sensor.

7. The method of claim 6, wherein determining that an amplification event has occurred comprises determining that the degree of similarity between the signals received from the first sensor and the signals received from the neighboring sensor is greater than a similarity threshold.

8. The method of claim 1, further comprising monitoring a temperature of the solution and/or the array, and controlling a signal to heating and/or cooling elements in thermal contact with the array based on the monitored temperature of the array.

9. The method of claim 8, further comprising detecting a plurality of amplification events, and monitoring the events as they occur to obtain and dynamically update a frequency value indicative of the rate of the reaction; and wherein controlling the signal to heating and cooling elements comprises using a closed feedback loop system to dynamically adjust the temperature based on the frequency value.

10. The method of claim 8, further comprising:

adjusting the temperature at the first sensor using the heating and/or cooling elements;

detecting a change in the signal from the first sensor responsive to the temperature adjustment; and adjusting the temperature at the first sensor based on the detected change.

11. The method of claim 1, wherein the method is performed during a nucleic acid amplification reaction.

12. The method of claim 11, wherein the nucleic acid amplification reaction is an isothermal reaction, and optionally wherein the reaction is a LAMP reaction.

13. The method of claim 1, wherein the biological sample is at least one of a DNA, RNA, or protein sample.

14. The method of claim 1, wherein the ion sensors are any of ISFET sensors, pH sensors, or chemically sensitive sensors.

15. The method of claim 1, wherein the method is a computer implemented method, and optionally wherein the method is carried out using an algorithm created using a machine learning technique.

16. A method of diagnosing a subject, the method comprising:

bringing a solution containing a biological sample into contact with an array of ion sensors;

determining that an amplification event has occurred in the vicinity of a first sensor of the array of ion sensors using the method of claim 1, the amplification event being indicative of the presence of a particular pathogen; and determining that the patient has a particular disease based on the presence of the pathogen.

* * * * *